United States Patent
Harvey et al.

(10) Patent No.: US 8,063,093 B2
(45) Date of Patent: Nov. 22, 2011

(54) POTASSIUM CHANNEL BLOCKERS AND USES THEREOF

(76) Inventors: Andrew J Harvey, Parkville (AU); Jonathan B Baell, Parkville (AU); Heike Wulff, Davis, CA (US)

( * ) Notice: Subject to any disclaimer, the term of this patent is extended or adjusted under 35 U.S.C. 154(b) by 918 days.

(21) Appl. No.: 11/886,210

(22) PCT Filed: Mar. 15, 2006

(86) PCT No.: PCT/AU2006/000333
§ 371 (c)(1),
(2), (4) Date: Mar. 18, 2008

(87) PCT Pub. No.: WO2006/096911
PCT Pub. Date: Sep. 21, 2006

(65) Prior Publication Data
US 2008/0221194 A1 Sep. 11, 2008

Related U.S. Application Data

(60) Provisional application No. 60/662,051, filed on Mar. 15, 2005.

(51) Int. Cl.
*A61K 31/407* (2006.01)
*C07D 491/02* (2006.01)

(52) U.S. Cl. .................................. 514/411; 548/432

(58) Field of Classification Search .................. 514/411; 548/432
See application file for complete search history.

(56) References Cited

U.S. PATENT DOCUMENTS

| 4,845,096 A | 7/1989 | Schlecker et al. |
| 5,039,701 A | 8/1991 | Schlecker et al. |

FOREIGN PATENT DOCUMENTS

| EP | 0284914 A1 | 10/1988 |
| EP | 0 303 920 B1 | 3/1992 |
| WO | WO03/078416 A1 | 9/2003 |

OTHER PUBLICATIONS

King, Med. Chem. Principle and Practice (1994), pp. 206-208).*

Levashova I. G., et al., "Reactivity of carbonyl derivatives of phenyl- and diphenylpropane. I. Kinetics of oxime formation from derivatives of furanochromone, dihydroflavanone, and chalcone", *Khimiya Priorodnykh Soedinenii 1*: 70-76 (1987), Abstract, Document No. 109:37644.

Martin M., et al., "Synthesis and β-adrenolytic properties of some amino alcohol derivatives of furo [3, 2-g] chrome", *European Journal of Medicinal Chemistry* 9(5): 563-570 (1974), Abstract, Document No. 83:9852.

Hamed Abu-Shady & Taito O. Soine, "Experiments with Khellin. II. The Synthesis of 5,6-Dimethoxy-2-methylfuro(2',3',7,8)chromone and Its Identity with Isokhellin", *J. Am. Pharm. Assoc. Am. Pharm. Assoc.* (Baltimore) 41(8):403-7 (1952).

* cited by examiner

*Primary Examiner* — Taofiq A Solola
(74) *Attorney, Agent, or Firm* — Scully, Scott, Murphy & Presser, P.C.

(57) ABSTRACT

The invention relates to compounds of Formula (1) for use in modulating potassium channel activity in cells.

20 Claims, No Drawings

POTASSIUM CHANNEL BLOCKERS AND USES THEREOF

FIELD OF THE INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Many autoimmune and chronic inflammatory diseases are related to immunoregulatory abnormalities. Diseases such as systemic lupus erythematosis, chronic rheumatoid arthritis, multiple sclerosis and psoriasis have in common the appearance of autoantibodies and self-reactive lymphocytes.

Multiple sclerosis is the most common neurological disease of young people. It is believed to cost more in medical care and lost income than any other neurological disease of young adults.

Multiple sclerosis affects the myelin sheaths of nerves. Myelin is an insulating material that coats most axons and allows rapid signal conduction over long distances by saltatory conduction. It is thought that antibodies and specialised cells of the immune system attack the myelin coating. This process leads to inflammation and scarring (sclerosis) which damages blood vessels in the area by the formation of a lesion known as a plaque. These plaques are characterised by being infiltrated by macrophages and T cells. This results in demyelination with the consequential loss of the rapid signal conduction.

A possible method of treating these autoimmune and inflammatory diseases is by suppressing T-cell proliferation and modulating their activation.

The early stages of T-cell activation may be conceptually separated into pre-$Ca^{2+}$ and post-$Ca^{2+}$ events (Cahalan and Chandy 1997, *Curr. Opin. Biotechnol.* 8 749). Following engagement of the T-cell receptor by an antigen, activation of tyrosine kinases and the generation of inositol 1,4,5-triphosphate lead to the influx of $Ca^{2+}$ and a rise in the cytoplasmic $Ca^{2+}$ concentration. The rise in $Ca^{2+}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{2+}$ signals while others require only a transient rise of $Ca^{2+}$.

Ion channels underlie the $Ca^{2+}$ signal of T-lymphocytes. $Ca^{2+}$ ions move across the plasma membrane through a channel termed the store-operated $Ca^{2+}$ channel or the calcium release-activated $Ca^{2+}$ channel. Two distinct types of potassium channels indirectly determine the driving force of calcium entry. The first is the voltage-gated Kv1.3 channel (Cahalan 1985, *J. Physiol.* 385: 197; Grissmer 1990, *Proc. Natl. Acad. Sci. USA* 87 9411; Verheugen 1995, *J. Gen. Physiol.* 105 765; Aiyar 1996, *J. Biol. Chem.* 271 31013; Cahalan and Chandy 1997, *Curr. Opin. Biotechnol.* 8 749) and the second is the intermediate-conductance calcium-activated potassium channel, IKCa1 (Grissmer 1993, *J. Gen. Physiol.* 102 601; Fanger 1999 *J. Biol. Chem.* 274 5746; Rauer 1999, *J. Biol. Chem.* 274 21885; VanDorpe 1998, *J. Biol. Chem.* 273 21542; Joiner 1997, *Proc. Natl. Acad. Sci. USA* 94 11013; Khanna 1999, *J. Bio. Chem.* 274 14838; Lodgson 1997, *J. Biol. Chem.* 272 32723; Ghanshani 1998, *Genomics* 51 160). When these potassium channels open, the resulting efflux of $K^+$ hyperpolarizes the membrane, which in turn accentuates the entry of $Ca^{2+}$, which is absolutely required for downstream activation events (Cahalan and Chandy 1997, *Curr. Opin. Biotechnol.* 8: 749).

The predominant voltage-gated channel in human T-lymphocytes is encoded by Kv1.3, a Shaker-related gene. Kv1.3 has been characterised extensively at the molecular and physiological level and plays a vital role in controlling T-lymphocyte proliferation, mainly by maintaining the resting membrane potential of resting T-lymphocytes. Inhibition of this channel depolarises the cell membrane sufficiently to decrease the influx of $Ca^{2+}$ and thereby prevents downstream activation events. Advantageously the Kv1.3 channel is almost exclusively located in T-lymphocytes.

Accordingly, compounds which are selective Kv1.3 blockers are potential therapeutic agents as immunosuppressants for the prevention of graft rejection, and the treatment of autoimmune and inflammatory disorders. They could be used alone or in conjunction with other immunosuppressants, such as selective IKCa1 blockers or cyclosporin, in order to achieve synergism and/or to reduce toxicity, especially of cyclosporin.

Developments in the field of voltage-gated K-channel electrophysiology have strengthened the case for treating of multiple sclerosis and also diabetes mellitus by inhibiting the Kv1.3 channel. It was found that autoreactive T-cells from multiple sclerosis patients exhibit highly elevated levels of Kv1.3 (Wulff, H et al (2003) J. Clin Invest. 111 (11) 1703-1713). ShK-K22Dap, a selective peptide blocker of Kv1.3, potently inhibited the proliferation of T-cells with this high-Kv1.3 phenotype. (Beeton, C. et al (2001) PNAS 98 13942-13947). The connection between T-cell replication and Kv1.3 blockade has also been shown through the use of a small molecule, a psoralen derivative, that is an active and relatively specific inhibitor of the Kv1.3 channel. The derivative showed specificity in inhibiting the proliferation of the high Kv1.3 T-cells over peripheral blood T-cells (Vennekamp et al (2004) Mol. Pharm. 65 1364-1374).

The Kv1.3 channel has also been associated with diabetes. Studies of Kv1.3 knockout mice found that the mice have increased insulin sensitivity. The selective blockage of the Kv1.3 channel also led to increased insulin sensitivity (Xu, J. et al. (2004) *PNAS* 101 (9), 3122-3117). It has been suggested by Wulff, who was involved in the electrophysiology on multiple sclerosis that diabetes also involves autoreactive T-cells that express very high levels of Kv1.3 (Wulff, H. et al. (2003) *Curr. Op. DDD.* 6 640-647).

At present there exist a number of non-selective potassium channel blockers that will inhibit lymphocyte proliferation, but have adverse side effects. Other potassium channels exist in a wide range of tissues including the heart and brain, and generally blocking these channels is undesirable. Accordingly it would be advantageous to provide or identify compounds, which are selective inhibitors of the Kv1.3 channel.

U.S. Pat. No. 5,494,895 discloses the use of a thirty-nine amino acid peptide, scorpion peptide margatoxin, as a selective inhibitor and probe of Kv1.3 channels present in human lymphocytes, and also as an immunosuppressant. However the use of this compound is limited by its potent toxicity.

International Patent Application publication No's WO 97/16438 and WO 09/716,437, and U.S. Pat. No. 6,051,590 describe the use of the triterpene, correolide and related compounds as immunosuppressants. The potential for these compounds to become immunosuppressants was illustrated by experiments showing their attenuation of the delayed-type hypersensitivity (DTH) response in mini-swine.

U.S. Pat. No. 6,077,680 describes DNA segments and proteins derived from sea anemone species, more particularly ShK toxin from Stichodactyla helianthus. The ShK toxin was found to block Kv1.1, Kv1.3, Kv1.4 and Kv1.6, but a mutant ShK-K22DAP found to selectively block Kv1.3. Unfortunately the mutant did not exhibit the requisite pharmacokinetic profile for clinical use. A recently reported ShK analog, ShK(L5), was at least 100-fold more active against Kv1.3 ($K_d$=69 pM) than Kv1.1 and furthermore it showed at least 250-fold selectivity over every other relevant member of the Kv1 family (Beeton et al. (2005) *Mol. Pharm.* In press).

Both ShK toxin and ShK(L5) were shown to both prevent and treat experimental autoimmune encephalomyelitis in Lewis rats, an animal model for human multiple sclerosis (Beeton, et al. (2001) *Proc. Natl. Acad. Sci. USA* 98 13942), by selectively targeting T-cells chronically activated by the myelin antigen, MBP (myelin basic protein). The same study also indicated that chronically activated encephalitogenic rat T-cells express a unique channel phenotype characterised by high expression of Kv1.3 channels (approximately 1500 per cell) and low numbers of IKCa1 channels (approximately 120 per cell). This channel phenotype is distinct from that seen in quiescent and acutely activated cells and may be a functionally relevant marker for chronically activated rat T lymphocytes.

Other compounds which are blockers of Kv1.3 include psoralens (Vennekamp et al. (2004) *Mol. Pharm.* 65, 1365-1374) and selected benzamides (Schalhofer et al. (2002) *Biochem.* 41, 7781-7794 and Schalhofer et al (2003) *Biochem.* 42, 4733-4743.

Khellinone, a substituted benzofuran and natural product from certain plants, and 8-Methoxypsoralen (8-MOP), both commercially available products, have been found to exhibit blocking activity on the Kv1.3 channel.

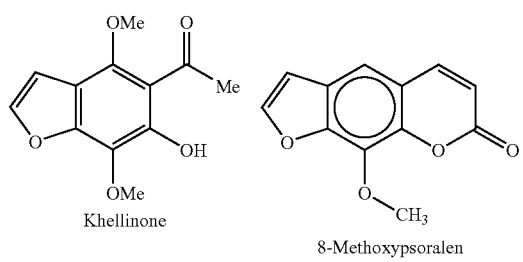

Khellinone

8-Methoxypsoralen

Khellinone, 8-MOP and four dimeric variants thereof were described in a Poster (abstract. No. 1078) at a meeting of the American Physiological Society in Snowmass, Colo. (*The Physiologist* 42: A12 (1999)). The authors were testing whether linking two active units with a spacer, improved activity. Some of the bivalent derivatives were said to be ineffective, and others were said to block the Kv1.3 channel, but lack therapeutic utility due to their extreme sensitivity to hydrolysis (very poor stability) and high lipophilicity (poor solubility in clinical conditions).

European Patent Application 82201051 describes furanochromone derivatives for use as anti-inflammatory agents amongst other suggested uses. An intermediate compound used in the manufacture of the chromone derivatives was 5-(benzoylacetyl)-4,7-dimethoxy-6-hydroxy-benzofuran.

European Patent Application 83302551 describes a process for preparing di-4,7-loweralkoxybenzofurans for use as intermediates in the preparation of khellin and related compounds.

German patent DE 3710469 and European patent publication number EP303920 describe the synthesis of 5-acetyl-4-benzyloxy-7-methoxy-6-hydroxy-benzofuran by alkaline ring cleavage of a pyrone ring of a fused system. This is also described in an article by Musante in Annali de Chimica (1959) 46, 768-781 together with the compound where the benzyloxy group is replaced with the residue of 2-hydroxyacetophenone.

An article by Bougery, G et al in J. Med. Chem (1981) 24, 159-167 described 4-alkoxy(ethoxy and iso-propoxy) khellinone derivatives for use as intermediates in the manufacture of other compounds.

An article by Musante, C and Fatutta, S in Farmaco Eduzione Scientifics (1961) 16, 343-350 described a 7-glucosyl-khellinone compound for use as a coronary dilator.

Articles by Abdel Hafez, O et al in Molecules (online computer file) (2001), 6(4), 396-405, by El-Hafez, O. in Bulletin of the Faculty of Pharmacy (Cairo University) (1996), 34(2), 111-117 and by Ragab, F. A. and Tawfeek, H in Eur. J. Med. Chem. (1987) 22(3), 265-267 describe assorted khellinone derivatives with assorted alkylamines at the 7 position.

PCT publication WO 03/078416 discloses dimers of assorted khellinone derivatives, linked via a spacer group. The spacer group is attached to the 6 position of each khellinone ring.

PCT publication WO 03/076407 discloses assorted khellinone derivatives which have been modified at the 5-position (the acyl group) to include a carbocyclic or heterocyclic ring.

SUMMARY OF THE INVENTION

In a first aspect the invention relates to compounds of the general formula I and salts thereof;

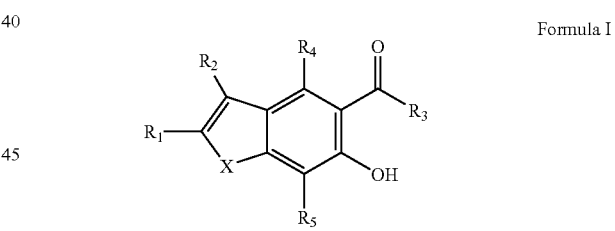

Formula I wherein $R_1$ and $R_2$ are independently selected from hydrogen, halo, $C_{1-6}$ alkyl, halo $C_{1-6}$ alkyl, phenyl and benzyl;

$R_3$ is an unsubstituted or halo substituted $C_{1-6}$ alkyl;

$R_4$ and $R_5$ are independently selected from $C_{1-10}$ alkyl, $C_{2-10}$ alkenyl; $C_{2-10}$ alkynyl, $C_{1-10}$ alkoxy, $C_{2-10}$ alkenyloxy and $C_{2-10}$ alkynyloxy;

and one of $R_4$ and $R_5$ is optionally substituted with one or more substituents selected from halo, aryl, aryloxy, heteroaryl and heteroaryloxy, the aryl, aryloxy, heteroaryl and heteroaryloxy substituents being optionally substituted;

and where the other of $R_4$ and $R_5$ is substituted with an aryl, aryloxy, heteroaryl or heteroaryloxy group, the group being optionally substituted, X is O, S or $NR_7$ where $R_7$ is independently selected from hydrogen, $C_{1-6}$ alkyl and halo $C_{1-6}$ alkyl;

provided that $R_4$ can not be unsubstituted benzyloxy when X is O, $R_1$ and $R_2$ are hydrogen, $R_3$ is methyl and $R_5$ is methoxy.

The term "alkyl" as used alone or in combination herein refers to a straight or branched chain saturated hydrocarbon group. The term "$C_{1-12}$ alkyl" refers to such a group containing from one to twelve carbon atoms and the terms "$C_{1-6}$ alkyl" and "lower alkyl" refer to such groups containing from one to six carbon atoms, such as methyl ("Me"), ethyl ("Et"), n-propyl, isopropyl, n-butyl, isobutyl, sec-butyl, tert-butyl and the like.

The term "$C_{3-7}$ cycloalkyl" refers to non-aromatic, saturated cyclic groups having from 3 to 7 carbon atoms. Examples include cyclopentyl and cyclohexyl.

The term "alkenyl" refers to a straight or branched hydrocarbon containing one or more double bonds, preferably one or two double bonds. The term "$C_{2-12}$ alkenyl" refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "$C_{4-7}$ cycloalkenyl" refers to non aromatic carbocycles having 4 to 7 carbon atoms and having one or more double bonds. Examples include cyclopentenyl, 1-methylcyclopentenyl, cyclohexenyl, 1,3-cyclopentadienyl, 1,3-cyclohexadienyl and 1,4-cyclohexadienyl.

The term "alkynyl" refers to a straight or branched hydrocarbon containing one or more triple bonds, preferably one or two triple bonds. The term "$C_{2-12}$ alkynyl" refers to such a group containing from two to twelve carbon atoms. Examples include 2-propynyl and 2- or 3-butynyl.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The terms "alkenyoxy" and "alkynyloxy" as used alone or in combination respectively refer to an alkenyl and alkynyl group as earlier described linked to the parent structure via an oxygen linkage (—O—).

The term "aromatic" when used alone or in combination refers to an unsubstituted or optionally substituted monocyclic or bicyclic aryl rings and ring systems (aromatic hydrocarbon rings or ring systems) and also aromatic heterocyclic rings or ring systems, as known as heteroaryl or heteroaromatic rings. Preferred aromatic rings are optionally substituted phenyl ("Ph") rings.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The terms "heterocyclic" and "heterocyclyl" refer to mono or bicyclic rings or ring systems that include one or more heteroatoms selected from N, S and O. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as furyl (also known as furanyl), thienyl and pyrrolyl rings.

The heterocyclic group may be attached to the parent structure through a ring carbon atom or through any heteroatom of the ring system that results in a stable structure. When fused to another ring, the ring atoms of the heterocyclic ring system includes the ring atoms of the fused ring and may be attached to the parent structure through one of the ring atoms of the fused ring.

Examples of 5-membered monocyclic heterocycles include furyl, thienyl, pyrrolyl, H-pyrrolyl, pyrrolinyl, pyrrolidinyl, oxazolyl, oxadiazolyl, (including 1, 2, 3 and 1, 2, 4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1, 2, 3 and 1,3,4-triazolyls), tetrazolyl, thiadiazolyl (including 1, 2, 3 and 1,3,4-thiadiazolyls). Examples of 6-membered monocyclic heterocycles include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl. The heterocycles may be optionally substituted with a broad range of substituents, such as $C_{1-6}$ alkyl, $C_{1-6}$ alkoxy, $C_{2-6}$ alkenyl, $C_{2-6}$ alkynyl, halo, hydroxy, mercapto, trifluoromethyl, phenyl, phenyloxy, phenylalkyl, phenylalkyloxy, amino, cyano or mono or di($C_{1-6}$alkyl)amino.

The heterocycle may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, cyano, phenyl, phenyloxy, phenylalkyl, phenylalkyloxy, amino and mono or di($C_{1-6}$alkyl)amino.

Examples of some preferred heterocyclic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines and quinoxalines. These heterocycles can be optionally substituted with, by example, $C_{1-6}$alkyl, $C_{1-6}$alkoxy, $C_{2-6}$alkenyl, $C_{2-6}$alkynyl, halo, hydroxy, mercapto, trifluoromethyl, amino, phenyl, phenyloxy, phenylalkyl, phenylalkyloxy, cyano or mono or di($C_{1-6}$alkyl)amino.

Examples of unsaturated 5-membered heterocyclic rings include oxazole, thiazole, imidazole, 1,2,3-triazole, isoxazole, isothiazole, pyrazole, furan, thiophene and pyrrole. Examples of unsaturated 6-membered heterocyclic rings include pyridine, pyrimidine, pyrazine, pyridazine and 1,2,4-triazine.

In a preferred embodiment, the heterocyclic ring is an aromatic ring. Heteroaryl and heteroaromatic are used to refer to this subset of heterocyclic rings. Heteroaryl rings include furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl.

Heteroaryl or heteroaromatic may preferably be selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

In another preferred embodiment, the heterocyclic ring is a non-aromatic ring selected from the group consisting of pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The term "aralkyl" refers to carbocyclic aromatic rings or ring systems as previously described and substituted by a alkyl group, also as previously described. Unless otherwise indicated the substituent is attached to the parent structure by the alkyl part of the substituent. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "halo alkyl" group has one or more of the hydrogen atoms on an alkyl group replaced with halogens. A notable example is —$CF_3$.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "optionally substituted" means that a group may include one or more substituents. One or more hydrogen atoms on the group may be replaced by substituent groups independently selected from halogens, $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$C_6H_4S(O)_qC_{1-6}$ alkyl, —$C(Ph)_3$, —CN, —OR, —O—$(CH_2)_{1-6}$—R, —O—$(CH_2)_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$;

where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, $C_{1-6}$ alkylaryl and $C_{1-6}$ alkylheterocyclyl, wherein the alkyl, alkenyl, alkynyl, cycloalkyl, cycloalkenyl, aryl, heterocyclyl, $C_{1-6}$ alkylaryl or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, cycloalkenyl, aryl or heterocyclyl group, the group may itself be optionally substituted with one to six of the same or different halogen atoms, hydroxy, lower alkyl, lower alkoxy, halo-$C_{1-6}$ alkyl (including —CF$_3$), phenyl, benzyl, —CN, —C(O)C$_{1-6}$ alkyl, mercapto, —NH$_2$, mono or di(lower alkyl)amino or —NO$_2$.

Examples of optional substituents include halogens, $C_{1-6}$ alkyl, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, —NH$_2$, —NHC$_{1-4}$ alkyl, —N(C$_{1-4}$ alkyl)$_2$, —CN, —NO$_2$, mercapto, C$_1$ alkylcarbonyl, $C_{1-6}$ alkoxycarbonyl and CO$_2$H.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of formula I, and the salts thereof, can be presented in the form of pharmaceutically acceptable derivatives. The term "pharmaceutically acceptable derivative" includes pharmaceutically acceptable esters, prodrugs, solvates and hydrates of the compounds of formula I or salts thereof. Pharmaceutically acceptable derivatives may include any pharmaceutically acceptable hydrate or any other compound or prodrug which, upon administration to a subject, is capable of providing (directly or indirectly) a compound of formula I or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a prodrug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of formula I of salt thereof.

It will be appreciated that the compounds of formula I and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

In some preferred embodiments of the invention, and with reference to the general formula I, one or more of the following preferred definitions apply:

a) $R_1$ and $R_2$ are selected from hydrogen, lower alkyl or halo, and are preferably hydrogen.

b) $R_3$ is unsubstituted $C_{1-6}$ alkyl, most preferably methyl.

Preferably, $R_1$ and $R_2$ are both hydrogen and $R_3$ is methyl.

c) One of $R_4$ and $R_5$ is $C_{1-10}$ alkyl, $C_{2-10}$ alkenyl, $C_{2-10}$ alkynyl, $C_{1-10}$ alkoxy, $C_{2-10}$ alkenyloxy, $C_{2-10}$ alkynyloxy. Preferably it is $C_{1-10}$ alkyl or $C_{1-10}$ alkoxy, more preferably $C_{1-10}$ alkoxy, more preferably lower alkoxy, more preferably methoxy or ethoxy and most preferably methoxy.

d) The other of $R_4$ and $R_5$ is a substituted $C_{1-10}$ alkyl or substituted $C_{2-10}$ alkoxy group, preferably a lower alkoxy group, more preferably a substituted methoxy or ethoxy group and most preferably a substituted methoxy group.

The substituent for the other of $R_4$ or $R_5$ is an optionally substituted aryl group, aryloxy, heteroaryl or heteroaryloxy group, preferably an optionally substituted aryloxy and most preferably optionally substituted phenoxy or napthoxy group.

It is preferable for the aryl, aryloxy, heteroaryl or heteroaryloxy group to be optionally substituted with 1 to 3 substituents independently selected from fluoro, chloro, bromo, lower alkyl, lower haloalkyl, lower alkoxy, lower haloalkoxy, nitro, hydroxyl, carboxyl, phenyl, napthyl, benzyl and benzoyl.

e) The other of $R_4$ and $R_5$ is a substituted $C_{1-10}$ alkoxy, and preferably a $C_{2-9}$ alkoxy, and more preferably a $C_2$, $C_3$, $C_4$, $C_5$, $C_6$ or $C_7$ alkoxy.

The substituent is an optionally substituted aryloxy or heteroaryloxy group. Preferably the substituent is an optionally substituted heteroaryloxy group and preferably the heteroaryl ring is a fused ring system. In a preferred embodiment the fused ring system is benzo[b]furanyl group.

The substituent may itself be optionally substituted with 1 to 4 substituents. The substituents may be independently selected from fluoro, chloro, bromo, lower alkyl, lower haloalkyl, lower alkoxy, lower haloalkoxy, nitro, hydroxyl, carboxyl, phenyl, naphthyl, benzyl and benzoyl.

It is preferred that the substituent is a benzo[b]furanyl of formula I, in which one of the groups at position 4, 6 or 7 (which corresponds to $R_4$, the hydroxy group or $R_5$) has been replaced with an oxo linkage.

In a preferred form, the other of $R_4$ and $R_5$ may be selected from formula IIa, IIb and IIc below:—

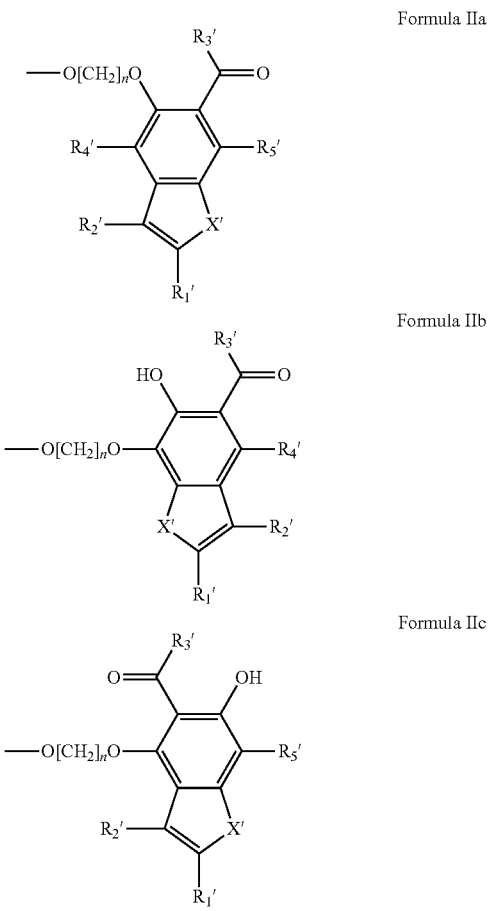

where n is 1 to 10, more preferably 3 to 7, most preferably 4, 5 or 6 and X', $R_1'$, $R_2'$, $R_3'$, $R_4'$ and $R_5'$ are independently as respectively defined for X, $R_1$, $R_2$, $R_3$, $R_4$ and $R_5$.

When the compound of formula I is a homodimer, the groups X', $R_1'$, $R_2'$, $R_3'$, $R_4'$ and $R_5'$ is respectively the same as X, $R_1$, $R_2$, $R_3$, $R_4$ and $R_5$.

When the compound of formula I is a mixed dimer, the groups X', $R_1'$, $R_2'$, $R_3'$, $R_4'$ and $R_5'$ are respectively selected from the definitions provided for X, $R_1$, $R_2$, $R_3$, $R_4$ and $R_5$ but may be different to the corresponding X, $R_1$, $R_2$, $R_3$, $R_4$ and $R_5$ group.

f) The other of $R_4$ and $R_5$ is —OCH$_2$—(C$_6$H$_4$)—CH$_2$O—Y, where Y is an optionally substituted aryl or heteroaryl group, preferably an optionally substituted heteroaryl group. Most preferably Y is an optionally substituted benzo[b]furanyl group.

Y may itself be optionally substituted with 1 to 4 substituents. The substituents may be independently selected from fluoro, chloro, bromo, lower alkyl, lower haloalkyl, lower alkoxy, lower haloalkoxy, nitro, hydroxyl, carboxyl, phenyl, naphthyl, benzyl and benzoyl.

It is preferred that Y is a benzo[b]furanyl of formula I, in which one of the groups at position 4, 6 or 7 (which corresponds to $R_4$, the hydroxy group or $R_5$) is replaced with a linking bond.

In a preferred variation, the other of $R_4$ and $R_5$ may be selected from formula IIIa, IIIb and IIIc below:—

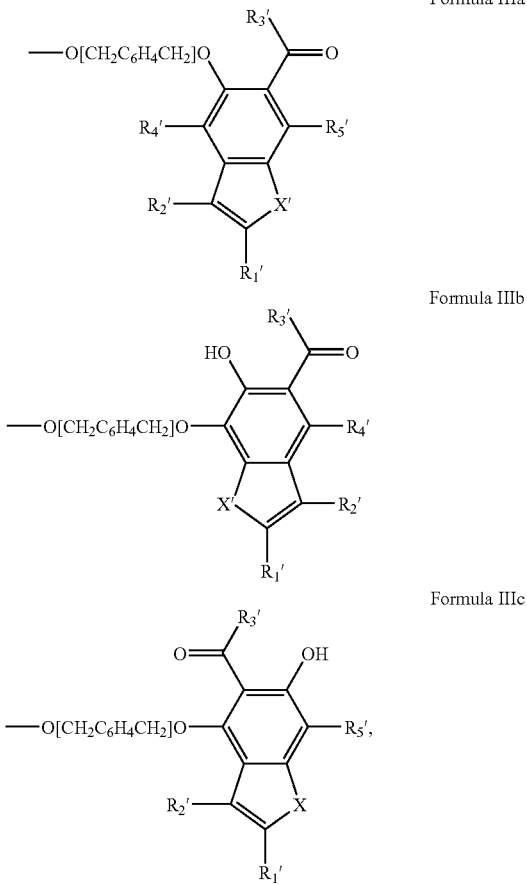

where n is 1 to 10, more preferably 3 to 7, most preferably 4, 5 or 6 and X', $R_1'$, $R_2'$, $R_3'$, $R_4'$ and $R_5'$ are independently as respectively defined for X, $R_1$, $R_2$, $R_3$, $R_4$ and $R_5$.

When the compound of formula I is a homodimer, the groups X', $R_1'$, $R_2'$, $R_3'$, $R_4'$ and $R_5'$ is respectively the same as X, $R_1$, $R_2$, $R_3$, $R_4$ and $R_5$.

When the compound of formula I is a mixed dimer, the groups X', $R_1'$, $R_2'$, $R_3'$, $R_4'$ and $R_5'$ are respectively selected from the definitions provided for X, $R_1$, $R_2$, $R_3$, $R_4$ and $R_5$ but may be different to the corresponding X, $R_1$, $R_2$, $R_3$, $R_4$ and $R_5$ group.

g) X is O.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds of formula I or pharmaceutically acceptable salt thereof, including pharmaceutically acceptable derivatives thereof, and optionally a pharmaceutically acceptable carrier or diluent.

In another aspect, the present invention provides pharmaceutical compositions for use as a Kv1.3 ion channel blocker, more particularly as an immunosuppressant, the composition comprising an effective amount of a compound of Formula I or pharmaceutically acceptable salt thereof, including pharmaceutically acceptable derivatives thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of compound of Formula I administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The compositions may further contain one or more other immunosuppressive compounds. For example the compositions may contain a second immunosuppressive agent such as azathioprine, brequinar sodium, deoxyspergualin, mizaribine, mycophenolic acid morpholino ester, cyclosporin, FK-506 and rapamycin.

The compounds of the present invention may be useful in the therapeutic or prophylactic treatment of the resistance to transplantation of organs or tissue (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases; rheumatoid arthritis, systemic lupus erythematosus, nephrotic syndrome lupus, Palmo-planter pustulosis, Hashimoto's thyroiditis, multiple sclerosis, Guillain-Barre syndrome, myasthenia gravis, type I diabetes uveitis, juvenile-onset or recent-onset diabetes mellitus, diabetic neuropathy, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Meniere's disease, polyneuritis, multiple neuritis, mononeuritis, radiculopathy, hyperthyroidism, Basedow's disease, pure red cell aplasia, aplastic anaemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T-cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Sjoegren's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Berger's disease, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and anti-inflammatory activity.

For certain of the abovementioned conditions it is clear that the compounds may be used prophylactically as well as for the alleviation of acute symptoms.

References herein to "treatment" or the like are to be understood to include such prophylactic treatment, as well as therapeutic treatments.

It is envisaged that the compounds may be particularly useful in the treatment of multiple sclerosis. This chronic neurological disorder affects the nerves of the central nervous system. As discussed earlier most nerves in the body are normally insulated by a protective sheath of fatty substance called myelin. Multiple sclerosis causes demyelination, in which this protective sheath becomes inflamed and ultimately destroyed.

By modulating or changing the immune system response that is thought to be responsible for the attack on the central nervous system it should be possible to attack the cause of the disease itself, rather than the more traditional method of controlling the symptoms.

The nature of the disease is such that it may be possible to control multiple sclerosis without unduly suppressing the patient's immune system. Based on the earlier discussed chronically activated human T-lymphocytes study, it is speculated that multiple sclerosis may be a product of chronically activated T-cells having a channel phenotype characterised by high expression of Kv1.3 channels and low numbers of IKCa1 channels. As this channel phenotype is distinct from that seen in quiescent and acutely activated cells it may provide a useful means for controlling multiple sclerosis without the significant side effects of less specific drugs.

Furthermore, in demyelinating diseases such as multiple sclerosis or diabetic neuropathy, the destruction of the myelin sheath evokes an internodal potassium current in myelinated nerve fibers by uncovering normally silent potassium channels. These abnormal potassium currents contribute to the conduction failure observed in demyelinated neurons. Blockers of axonal potassium channels such as the unselective compound 4-aminopyridine (4-AP) have been demonstrated to overcome conduction failure in vitro and to improve disability in certain multiple sclerosis patients. 4-AP (Fampridine) is currently in clinical trials for multiple sclerosis. Compounds that block both the Kv1.3 channel in autoreactive T-cells and the Kv1.1-Kv1.2 heteromultimeric channels present in the Ranvier Nodes of myelinated nerves might be ideally suited for the treatment of multiple sclerosis. Such compounds could simultaneously enhance impulse propagation in demyelinated neurons and modify the immune response.

Thus in another aspect of the invention there is provided a method of preventing or treating autoimmune or chronic inflammatory diseases, the prevention of rejection of foreign organ transplants and/or related afflictions, said method including the step of administrating a compound of formula I, or salt thereof, including a pharmaceutically acceptable derivative thereof, or a composition comprising the compound or salt thereof, or a pharmaceutically acceptable derivative thereof.

Accordingly in a preferred form of the invention, there is provided a means for controlling multiple sclerosis by the application of a blocker of the Kv1.3 channel, preferably a selective channel blocker of the Kv1.3 channel, and optionally also a blocker of Kv1.1 and/or Kv1.2 channels, by the application of a compound of formula I or salt thereof, including a pharmaceutically acceptable derivative thereof, or a composition comprising the compound of formula I or salt thereof, or a pharmaceutically acceptable derivative thereof.

In another preferred form of the invention there is provided a method for preventing or treating diabetes including the step of administrating a compound of formula I or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect, the invention provides a method of modulating potassium ion channel activity of T-cells by the application of a compound of Formula I or a pharmaceutically acceptable salt thereof, including a pharmaceutically acceptable derivative thereof, or a composition comprising the same, to said T cells. Preferably the compounds of the invention inhibit the potassium ion channel activity of T-cells.

Preferably the potassium channel activity inhibited by the compound of Formula I is a voltage-gated potassium channel, for example, Kv1.1-Kv1.7. More preferably the potassium ion channel activity is the voltage-gated potassium channel, Kv1.3 of a T-cell. Preferably the compound selectively inhibits the Kv1.3 channel, and optionally also the Kv1.1 and/or Kv1.2 channels.

In a further aspect of the present invention, there is provided the use of a compound of formula I or salt thereof, including a pharmaceutically acceptable derivative thereof, in the preparation of a medicament for the treatment (therapeutic or prophylactic) of disease states mediated by potassium channels, and in particular by blocking the Kv1.3 channel.

In a further aspect of the invention there is provided a process for the production of the compounds of Formula I or salts thereof, including pharmaceutically acceptable derivatives thereof.

The compounds of the invention can be made from khellin, a natural product from plants which is cheap and commercially available. A general synthetic scheme is set out below for those compounds where $R_4$ and $R_5$ includes an oxygen atom linking it to the parent structure:—

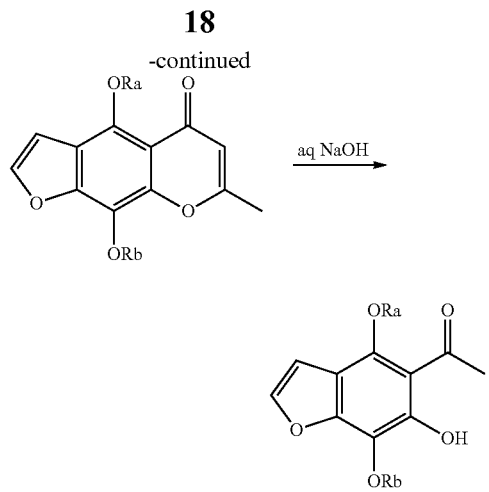

Where L is a halide leaving group and $R_a$ and $R_b$ are independently selected from $C_{1-10}$ alkyl, $C_{2-10}$ alkenyl and $C_{2-10}$ alkynyl, $C_{1-10}$ alkoxy, $C_{2-10}$ alkenyloxy and $C_{2-10}$ alkynyloxy;

and one of $R_a$ and $R_b$ is optionally substituted with one or more substituents selected from halo, aryl, aryloxy, heteroaryl and heteroaryloxy, the aryl, aryloxy, heteroaryl and heteroaryloxy, the substituents being optionally substituted;

and where the other of $R_a$ and $R_b$ is substituted with aryl, aryloxy, heteroaryl or heteroaryloxy group, the group being optionally substituted.

The vinylogous ester containing six-membered ring of khellin acts as a protecting group for the ultimate phenol and acetyl functionalities during the manipulations of the ethers. An alternate synthesis from khellinone can be envisaged where the phenol at the 6-position is capped with a suitable protecting group.

Compounds of the invention where $R_a$ is other than Me may be synthesised in accordance with the following scheme.

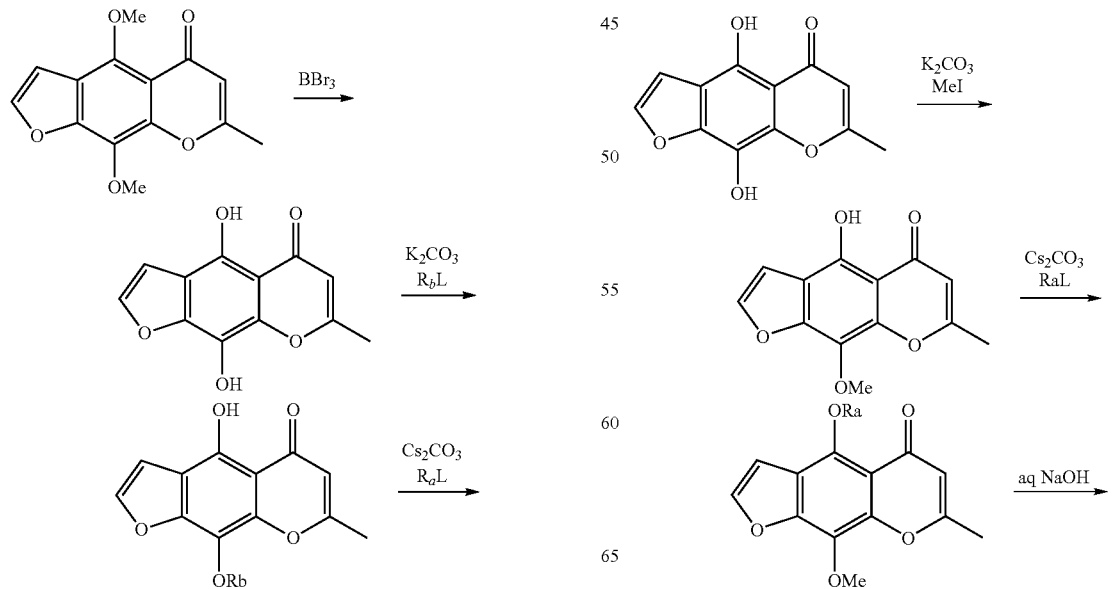

The 4,4 linked dimers of the invention may be synthesised in accordance with the following scheme.

The linker can be any suitable group, which has bis halo substitution with a suitable halide leaving group L, such as Bromine. The linker can be L-(CH$_2$)$_n$-L, substituted forms thereof and can be L-CH$_2$—C$_6$H$_4$—CH$_2$-L.

Compounds of the invention where R$_b$ is other than Me may be synthesised in accordance with the following scheme. This scheme is preferred when the reaction with the alkyl halide is facile.

The alternative reaction scheme is preferred when the reaction with alkyl halide is slow, either due to the low reactivity of alkyl halides such as alkyl chlorides or due to the requirement of two consecutive alkylations when forming dimers. The scheme begins with the preparation of 7-desmethylkhellin, which can then be used to prepare the compounds of the invention.

Synthesis of intermediate 7-desmethylkhellin

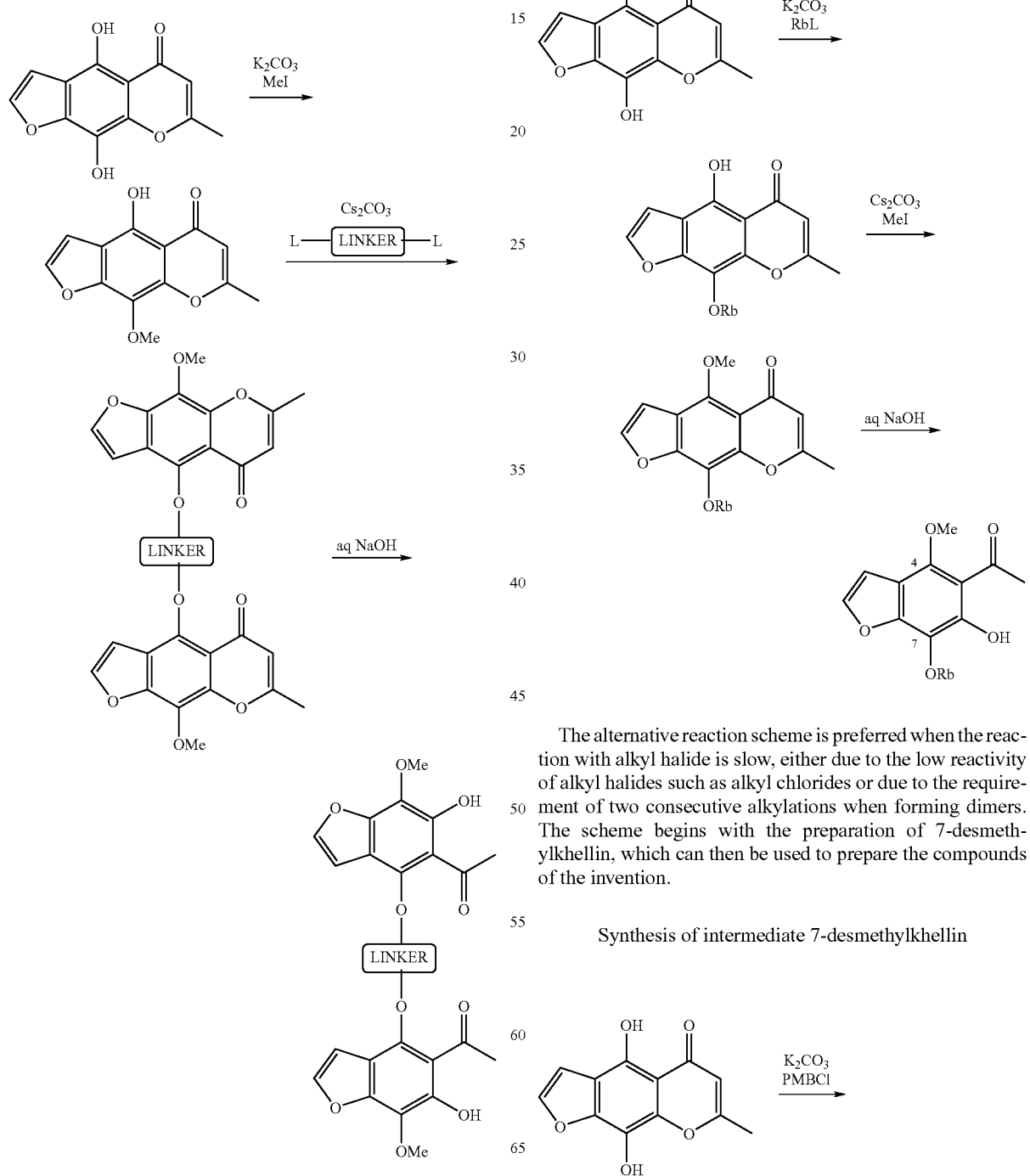

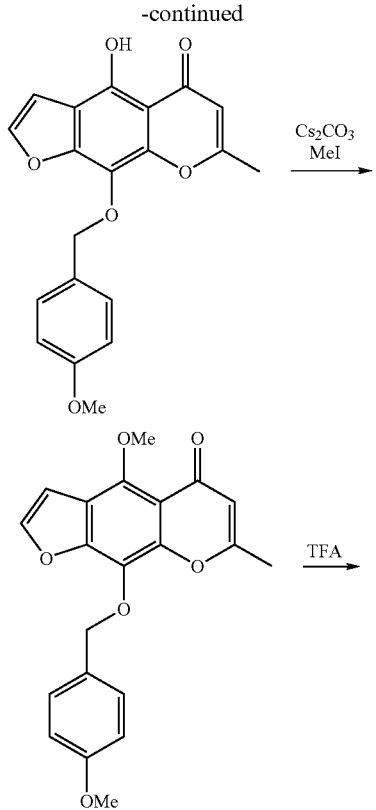

Synthesis of compounds of formula I when $R_b$ is other than Me.

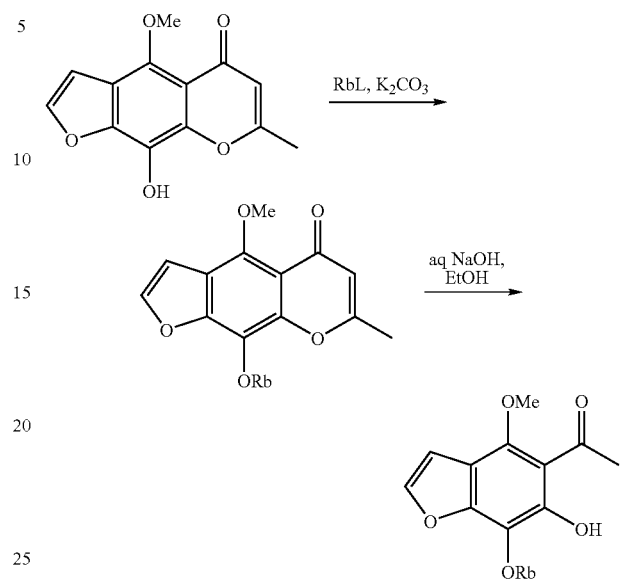

A preferred embodiment of 7-alkoxykhellinones is any aryl-$(CH_2)_n$—O— substituted example ($R_b$ is Ar—$(CH_2)_n$—, where n is 1 to 7). An alternative synthesis for this subset of compounds is shown below. Sonogashira coupling of 7-alkynyl khellin with an aryl iodide may furnish an aryl alkyne, which upon hydrogenation, reoxidation of the benzofuran, and hydrolysis may afford the desired aryl-$(CH_2)_n$—O-khellin. Heck coupling of 7-allyl khellin offers an alternate pathway to this class of compounds. Suitable coupling agents are known in the art and include $Pd(PPh_3)_2Cl_2$, $Pd(PPh_3)_4$, Pd(dibenzylideneacetone), and $PdCl_2(CH_3CN)_2$. Preferably the palladium catalysed coupling reactions include a co-catalyst, for instance, CuI, in the presence of a suitable base such as a trialkylamine base.

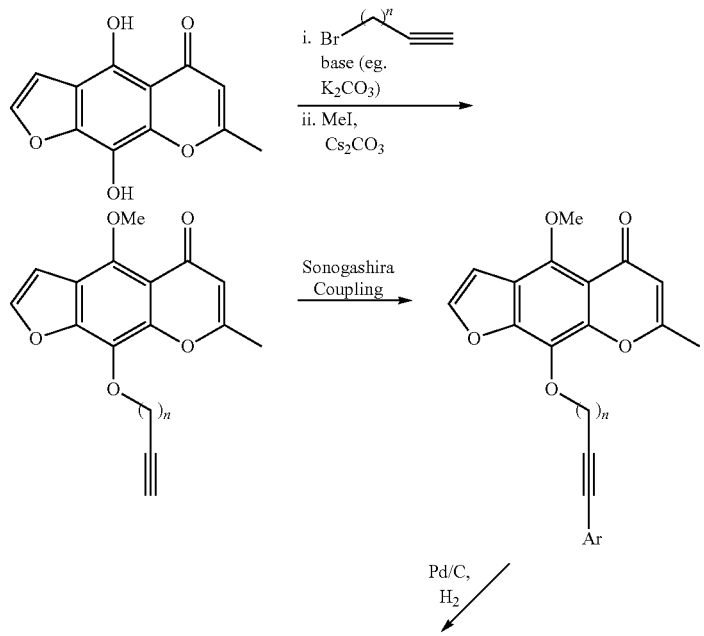

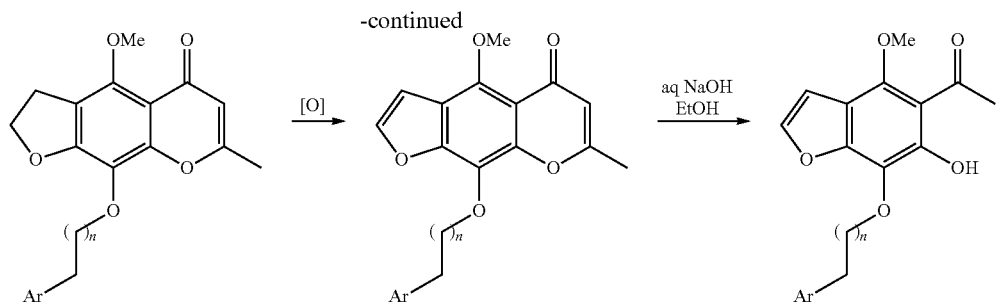
Synthesis of 7,7 linked dimers of formula I.
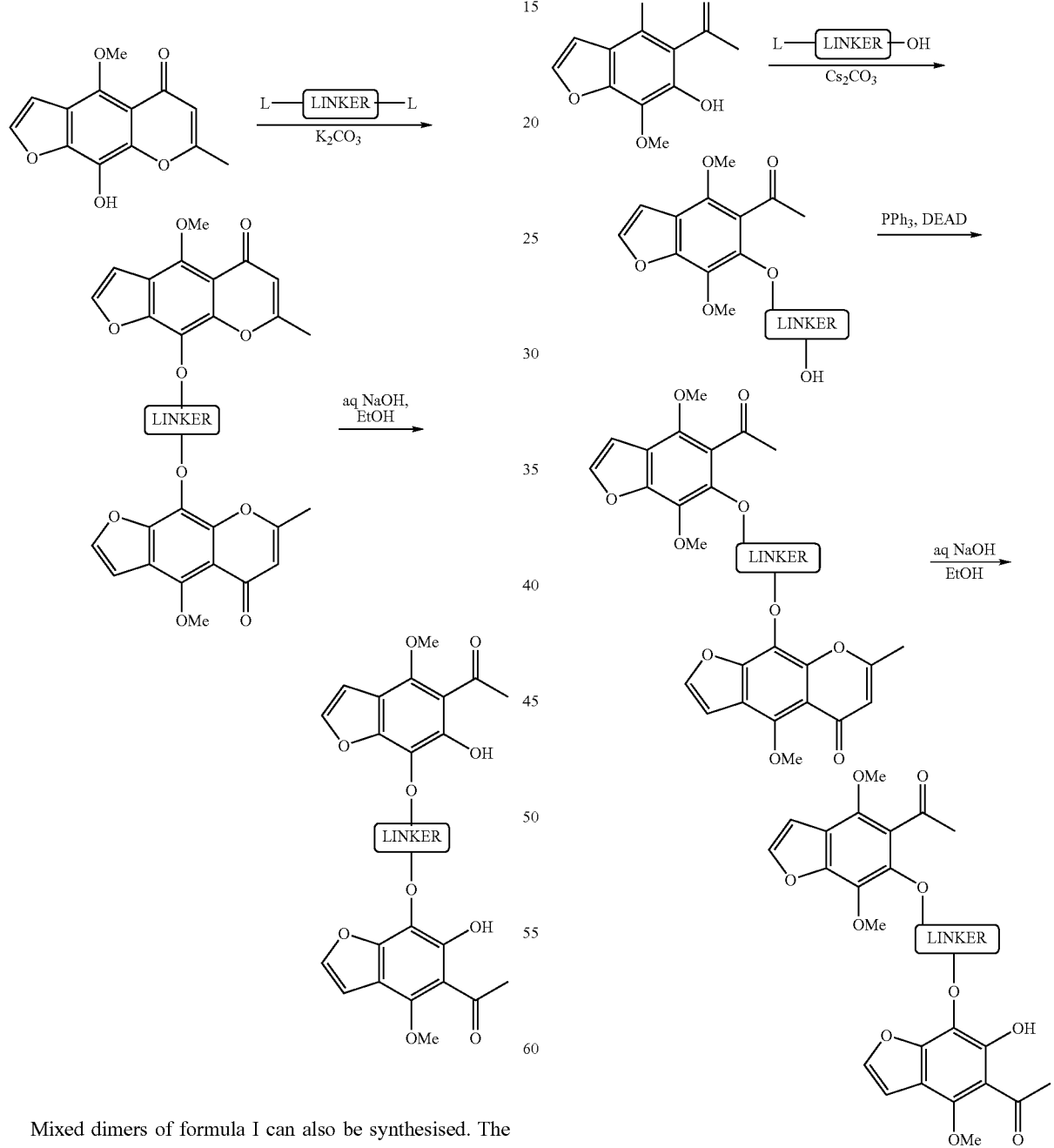
Mixed dimers of formula I can also be synthesised. The following scheme depicts the method of preparing a 7,6 linked dimer of formula I. Similar methods can be used to prepare the other mixed dimers.
A bifunctional linker precursor is reacted through its alkyl halide with one molecule of khellinone or a derivative thereof.

Then the second linker functional group, an alcohol, is employed as a nucleophile in a Mitsunobu reaction with a different khellinone derivative to give the mixed dimer.

Alternatively it may be possible to mix two or more different khellinone derivatives may be mixed together and subsequently reacted with a linker compound in basic conditions to form a mixture of products that are then separated or used in combination. This approach may have difficulties depending on the nucleophilicities of each phenol.

4-alkyl or 7-alkyl khellinones may be synthesised by the following prophetic schemes.

| TFA | trifluoroacetic acid |
| PMBCl | para methoxybenzyl chloride |
| DEAD | diethylazodicarboxylate |
| Aq | aqueous |
| Tf$_2$O | triflic anhydride |

Another variation is to add, remove or modify the substituents of the product to form new derivatives. This could be achieved by using standard techniques for functional group

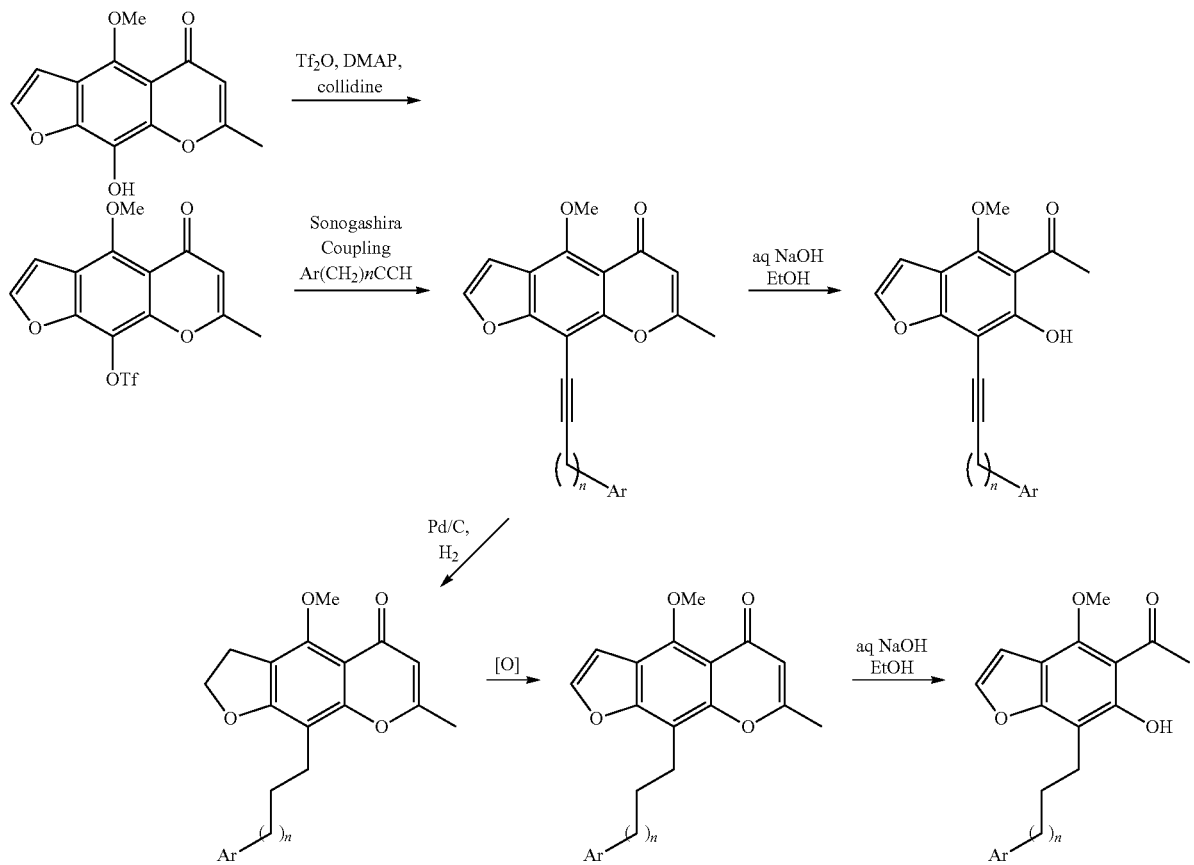

Starting with 7-triflyl khellin (or the 7-bromo visnagin (not shown)) Sonogashira coupling with an alkyne may provide the disubstituted alkyne. Reduction of the alkyne, followed by selective oxidation and alkaline hydrolysis, may give the 7-alkyl khellinone. Note that an analogous preparation could be envisaged for the generation of 4-alkyl khellinones starting from 4-triflyl khellin.

These schemes may be used to synthesise compounds where one or both of $R_4$ and $R_5$ are independently selected from $C_{1-10}$ alkyl, $C_{2-10}$ alkenyl and $C_{2-10}$ alkynyl;

and one of $R_4$ and $R_5$ is optionally substituted with one or more substituents selected from halo, aryl, aryloxy, heteroaryl and heteroaryloxy, the aryl, aryloxy, heteroaryl and heteroaryloxy substituents being optionally substituted;

and where the other of $R_4$ and $R_5$ is substituted with aryl, aryloxy, heteroaryl or heteroaryloxy group, the group being optionally substituted.

In the above schemes the following abbreviations were used:— inter-conversion, well known in the industry such as those described in Comprehensive organic transformations: a guide to functional group preparations by Larock R C, New York, VCH Publishers, Inc. 1989.

Examples of possible functional group inter-conversions are: —C(O)NRR' from —CO$_2$CH$_3$ by heating with or without catalytic metal cyanide, e.g. NaCN, and HNRR' in CH$_3$OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R") SR''' with H$_3$NR$^+$OAc by heating in alcohol; —C(NR'R")SR from —C(S)NR'R" with R—I in an inert solvent, e.g. acetone; —C(S)NR'R" (where R' or R" is not hydrogen) from —C(S)NH$_2$ with HNR'R"; —C(=NCN)—NR'R" from —C(=NR'R")—SR with NH$_2$CN by heating in anhydrous alcohol, alternatively from —C(=NH)—NR'R" by treatment with BrCN and NaOEt in EtOH; —NR—C(=NCN)SR from —NHR' by treatment with (RS)₂C=NCN; —NR"SO₂R from —NHR' by treatment with ClSO₂R by heating in pyridine; —NR'C(S)R from —NR'C(O)R by treatment with Lawesson's reagent [2,4-bis(4-methoxyphenyl)-1,3,2,4-dithiadiphosphetane-2,4-disulfide]; —NRSO₂CF₃ from —NHR with triflic anhydride and base, —CH(NH₂)CHO from —CH(NH₂)C(O)OR' with Na(Hg) and HCl/EtOH; —CH₂C(O)OH from —C(O)OH by treatment with SOCl₂ then CH₂N₂ then H₂O/Ag₂O; —C(O)OH from —CH₂C(O)OCH₃ by treatment with PhMgX/HX then acetic anhydride then CrO₃; R—OC(O)R' from RC(O)R' by R"CO₃H; —CCH₂OH from —C(O)OR' with Na/R'OH; —CHCH₂ from —CH₂CH₂OH by the Chugaev reaction; —NH₂ from —C(O)OH by the Curtius reaction; —NH₂ from —C(O)NHOH with TsCl/base then H₂O; —CHC(O)CHR from —CHCHOHCHR by using the Dess-Martin Periodinane regent or CrO₃/aqH₂SO₄/acetone; —C₆H₅CHO from —C₆H₅CH₃ with CrO₂Cl₂; —CHO from —CN with SnCl₂/HCl; —CN from —C(O)NHR with PCl₅; —CH₂R from —C(O)R with N₂H₄/KOH.

It will be appreciated by those skilled in the art from the above schemes that one of the key intermediates in forming the compounds of formula I is the corresponding Khellin.

Accordingly, in another aspect the present invention provides a process for preparing a compound of formula I or a salt thereof, comprising subjecting a compound of formula VI

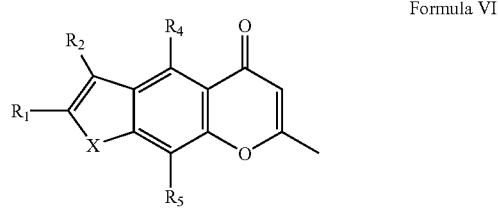

Formula VI to alkaline hydrolysis for a time and under conditions sufficient to form a compound of formula I, wherein $R_1$, $R_2$, $R_4$ and $R_5$ are as defined above for the compounds of formula I.

Also, apart from the Khellins of formula VI serving as key synthetic intermediates for the compounds of formula I, some intermediates may also possess useful biological activity akin to that which has been described above for the compounds of formula I.

Thus, another aspect of the invention relates to the compounds of formula VI:

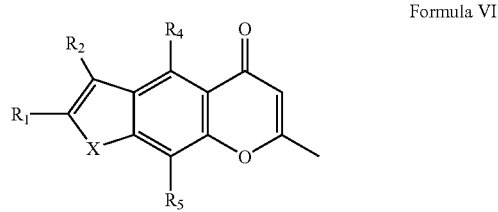

Formula VI or a salt thereof,
wherein $R_1$ and $R_2$ are independently selected from hydrogen, halo, $C_{1-6}$ alkyl, halo $C_{1-6}$ alkyl, phenyl and benzyl;
$R_4$ and $R_5$ are independently selected from $C_{1-10}$ alkyl, $C_{2-10}$ alkenyl; $C_{2-10}$ alkynyl, $C_{1-10}$ alkoxy, $C_{2-10}$ alkenyloxy and $C_{2-10}$ alkynyloxy;

and one of $R_4$ and $R_5$ is optionally substituted with one or more substituents selected from halo, aryl, aryloxy, heteroaryl and heteroaryloxy, the aryl, aryloxy, heteroaryl and heteroaryloxy substituents being optionally substituted;

and where the other of $R_4$ and $R_5$ is substituted with an aryl, aryloxy, heteroaryl or heteroaryloxy group, the group being optionally substituted, X is O, S or $NR_7$ where $R_7$ is independently selected from hydrogen, $C_{1-6}$ alkyl and halo $C_{1-6}$ alkyl;

provided that $R_4$ can not be unsubstituted benzyloxy when X is O, $R_1$ and $R_2$ are hydrogen and $R_5$ is methoxy.

Preferred compounds of the compounds of formula VI are the same as defined herein for the compounds of formula I.

In order that the present invention may be more readily understood, we provide the following non-limiting examples.

EXAMPLES

GENERAL PROCEDURE

A. 4-substituted khellinone derivatives

The khellinone derivatives which were substituted at the 4 position (R4) were generally synthesised in accordance with the following general reaction scheme.

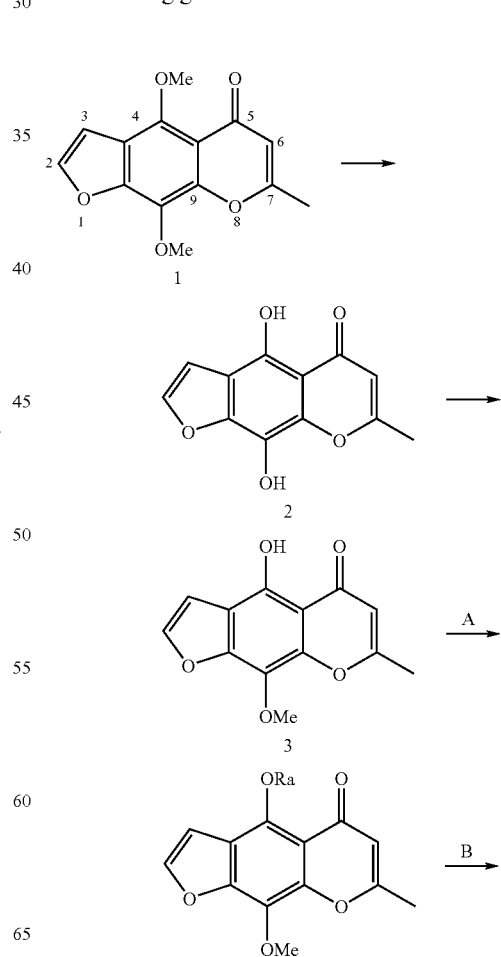

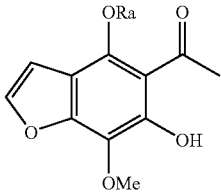

Intermediate 2

4,9-Dihydroxy-7-methyl-furo[3,2-g]chromen-5-one

Boron tribromide (1M in dichloromethane, 80 mL, 80 mmol) was added to a suspension of khellin 1 (10.4 g, 40 mmol) in dichloromethane (100 mL) at −78° C. over 75 min. The reaction mixture was allowed to warm to room temperature (rt) then was stirred at rt for 16 h. On cooling the reaction mixture to 0° C., the reaction was quenched with water by dropwise addition at first, but at an increasing rate until 50 mL had been added. The reaction mixture was concentrated in vacuo to remove the dichloromethane and the resulting suspension was filtered, washing with water. The orange solid was heated as a suspension in propan-2-ol (200 mL) at 70° C. for 20 min, during which time the solid became pale yellow. The suspension was filtered and the solid was dried to afford 2 (8.4 g, 90%) as a pale yellow solid.

Mp 283-284° C.; $^1$H NMR (d$_6$-DMSO) δ: 2.42 (s, 3H), 6.19 (s, 1H), 7.05 (d, J=2.1 Hz, 1H), 8.02 (d, J=2.1 Hz, 1H), 9.84 (br s, 1H), 12.9 (s, 1H); $^{13}$C NMR (d$_6$-DMSO) δ: 20.2, 104.4, 105.1, 107.0, 112.9, 123.3, 141.8, 145.7, 146.3, 148.2, 168.5, 183.9; MS (ES+) m/z 233.2 (M+H$^+$).

Intermediate 3

4-hydroxy-9-methoxy-7-methyl-furo[3,2-g]chromen-5-one

K$_2$CO$_3$ (2.76 g, 20 mmol) and dimethylsulfate (1.00 mL, 10.5 mmol) was added to a solution of 2 (2.32 g, 10 mmol) in acetonitrile (45 mL) and the reaction mixture was stirred at 80° C. for 90 min. The reaction was quenched by addition of 10% aqueous citric acid solution (30 mL) followed by 15 min stirring at rt. The reaction mixture was then concentrated to half volume and the resulting suspension was partitioned over chloroform (100 mL) and 10% citric acid solution (100 mL). The phases were separated and the aqueous phase was extracted with chloroform (2×100 mL) to give 3 (2.33 g, 95%) as a yellow solid.

Mp 201-202° C.; $^1$H NMR (d$_6$-DMSO) δ: 2.46 (s, 3H), 4.04 (s, 3H), 6.30 (s, 1H), 7.13 (d, J=2.1 Hz, 1H), 8.09 (d, J=2.1 Hz, 1H); $^{13}$C NMR (d$_6$-CDCl$_3$) δ: 20.7, 61.8, 104.7, 105.6, 107.8, 113.8, 125.9, 114.9, 145.4, 149.9, 151.0, 167.4, 184.2; MS (ES$^+$) m/z 247.2 (M+H$^+$).

General Procedure A Alkylation of 9-methylkhellin

A suspension of 3 (1.0 equiv.), caesium carbonate (2.0 equiv.) and alkyl or benzyl halide (1.2 equiv.) in anhydrous dimethylformamide (0.2 M) was stirred under nitrogen at rt until completion as determined by TLC (typically 16 h). The reaction mixture was then diluted with ethyl acetate and washed with 2M HCl (twice) and brine, dried (MgSO$_4$), and concentrated in vacuo. The crude was purified by flash chromatography.

General Procedure B Hydrolysis of 4-methyl-9-alkylkhellin

To a solution of the khellin analogue in ethanol (2 parts, 0.01-0.1 M) at reflux was added slowly 3M NaOH (1 part) and the resulting solution was stirred at reflux for 3 h. The reaction mixture was concentrated in vacuo to one third of the original volume and then acidified to pH2 by Universal indicator with 2M HCl. If precipitation occurred, the solid was collected by filtration washing with water. The solid was then dried in the presence of P$_2$O$_5$. If precipitation did not occur the acidified reaction mixture was extracted with ethyl acetate (twice) and the pooled organics were washed with brine, dried (MgSO$_4$) and concentrated in vacuo.

The following examples were prepared by the above method.

TABLE 1

Preparation of 4-substituted khellinones of formula I (X = O, R$_1$ = R$_2$ = H, R$_3$ = Me, R$_5$ = OMe, R$_4$ = ORa)

| Compd | Ra | Yield from 3 | Mp ° C. | MS | $^1$H NMR (CDCl$_3$) δ: |
|---|---|---|---|---|---|
| 4 | 1-naphthylmethyl | 27% | 96-98 | 363.0 ES$^+$ (M + H) | 2.41 (s, 3H), 4.06 (s, 3H), 5.80 (s, 2H), 6.78 (d, 1H), 7.46-7.56 (m, 4H), 7.89 (m, 2H), 8.00 (d, 1H) |
| 5 | 2-naphthylmethyl | 31% | 126-127 | 363.0 ES$^+$ (M + H) | 2.65 (s, 3H), 4.08 (s, 3H), 5.49 (s, 2H), 6.84 (d, 1H), 7.49-7.56 (m, 4H), 7.85-7.93 (m, 4H), 13.03 (s, 1H) |
| 6 | benzyl | 62% | 93-94 | 313.0 ES$^+$ (M + H) | 2.63 (s, 3H), 4.07 (s, 3H), 5.33 (s, 2H), 6.80 (d, 1H), 7.42 (m, 5H), 7.50 (d, 1H), 13.00 (s, 1H) |
| 7 | phenethyl | 23% | 86-88 | 323.1 ES$^+$ (M + H) | 2.62 (s, 3H), 3.18, (t, 2H), 4.04 (s, 3H), 4.52 (t, 2H), 6.64 (d, 1H), 7.25-7.37 (m, 5H), 7.45 (d, 1H), 13.03 (s, 1H) |
| 8 | phenylpropyl | 60% | 94-95 | 341.0 ES$^+$ (M + H) | 2.23 (m, 2H), 2.77, (s, 3H), 2.87 (t, 2H), 4.04 (s, 3H), 4.33 (t, 2H), 6.72 (d, 1H), 7.21-7.35 (m, 5H), 7.46 (d, 1H), 13.06 (s, 1H) |
| 9 | phenylbutyl | 51% | 121-122 | 355.0 ES$^+$ (M + H) | 1.88 (m, 4H), 2.69 (m, 5H), 4.05 (s, 3H), 4.29 (t, 2H), 6.77 (d, 1H), 7.19-7.31 (m, 5H), 7.45 (d, 1H), 13.06 (s, 1H) |

TABLE 1-continued

Preparation of 4-substituted khellinones of formula I (X = O, $R_1$ = $R_2$ = H, $R_3$ = Me, $R_5$ = OMe, $R_4$ = ORa)

| Compd | Ra | Yield from 3 | Mp °C. | MS | $^1$H NMR (CDCl$_3$) δ: |
|---|---|---|---|---|---|
| 10 | phenylpentyl | 61% | N/A | 369.3 ES$^+$ (M + H) | 1.52 (m, 2H), 1.74 (m, 2H), 1.88 (m, 2H), 2.66 (t, 2H), 2.70 (s, 3H), 4.02 (s, 3H), 4.29 (t, 2H), 6.80 (d, 1H), 7.16-7.28 (m, 5H), 7.46 (d, 1H) |
| 11 | 2-fluorobenzyl | 38% | 105-108 | 330.9 ES$^+$ (M + H) | 2.63 (s, 3H), 4.06 (s, 3H), 5.33 (s, 2H), 6.85 (d, 1H), 7.10-7.21 (m, 2H), 7.37-7.47 (m, 2H), 7.50 (d, 1H) |
| 12 | 2-chlorobenzyl | 46% | 84-86 | 346.9 ES$^+$ (M + H) | 2.63 (s, 3H), 4.08 (s, 3H), 5.40 (s, 2H), 6.75 (d, 1H), 7.31-7.34 (m, 2H), 7.43-7.56 (m, 1H) |
| 13 | 2-methylbenzyl | 27% | 101-103 | 325.3 ES$^-$ (M − H) | 2.36 (s, 3H), 2.55 (s, 3H), 4.05 (s, 3H), 5.32 (s, 2H), 6.74 (d, 1H), 7.20-7.30 (m, 3H), 7.39 (d, 1H), 7.46 (d, 1H) |
| 14 | 2-phenylbenzyl | 43% | 126-127 | 388.9 ES$^+$ (M + H) | 2.56 (s, 3H), 4.02 (s, 3H), 5.24 (s, 2H), 6.39 (d, 1H), 7.29-7.45 (m, 9H), 7.59 (m, 1H) |
| 15 | 3-fluorobenzyl | 56% | 118-121 | 330.9 ES$^+$ (M + H) | 2.63 (s, 3H), 4.05 (s, 3H), 5.28 (s, 2H), 6.73 (d, 1H), 7.06-7.19 (m, 3H), 7.37 (m, 1H), 7.48 (d, 1H) |
| 16 | 3-chlorobenzyl | 66% | 108-111 | 345.4 ES$^-$ (M − H) | 2.63 (s, 3H), 4.09 (s, 3H), 5.25 (s, 2H), 6.72 (d, 1H), 7.26-7.36 (m, 3H), 7.45 (s, 1H), 7.51 (d, 1H) |
| 17 | 3-methylbenzyl | 62% | 99-101 | 326.9 ES$^+$ (M + H) | 2.37 (s, 3H), 2.62 (s, 3H), 4.05 (s, 3H), 5.26 (s, 2H), 6.78 (d, 1H), 7.17-7.32 (m, 4H), 7.47 (d, 1H) |
| 18 | 3-methoxybenzyl | 17% | 97-99 | 341.3 ES$^-$ (M − H) | 2.65 (s, 3H), 3.80 (s, 3H), 4.05 (s, 3H), 5.30 (s, 2H), 6.79 (d, 1H), 6.90-7.01 (m, 3H), 7.34 (t, 1H), 7.49 (d, 1H), 13.00 (s, 1H) |
| 19 | 3-trifluoromethoxybenzyl | 62% | 86-88 | 396.9 ES$^+$ (M + H) | 2.62 (s, 3H), 4.06 (s, 3H), 5.30 (s, 2H), 6.72 (d, 1H), 7.22-7.49 (m, 5H) |
| 20 | 3-nitrobenzyl | 35% | 160-162 | 356.2 ES$^-$ (M − H) | 2.64 (s, 3H), 4.07 (s, 3H), 5.37 (s, 2H), 6.70 (d, 1H), 7.50 (d, 1H), 7.62 (t, 1H), 7.77 (d, 1H), 8.25 (d, 1H), 8.34 (s, 1H) |
| 21 | 4-fluorobenzyl | 35% | 100-102 | 329.4 ES$^-$ (M − H) | 2.59 (s, 3H), 4.05 (s, 3H), 5.26 (s, 2H), 6.76 (d, 1H), 7.09 (m, 2H), 7.38 (m, 2H), 7.48 (d, 1H) |
| 22 | 4-chlorobenzyl | 35% | 106-108 | 345.3 ES$^-$ (M − H) | 2.61 (s, 3H), 4.06 (s, 3H), 5.27 (s, 2H), 6.75 (d, 1H), 7.38 (m, 4H), 7.49 (d, 1H), 12.94 (s, 1H) |
| 23 | 4-bromobenzyl | 10% | 98-101 | 389.4 391.3 ES$^-$ (M − H) | 2.62 (s, 3H), 4.07 (s, 3H), 5.26 (s, 2H), 6.75 (d, 1H), 7.30 (m, 2H), 7.50 (d, 1H), 7.55 (m, 2H), 12.94 (s, 1H) |
| 24 | 4-trifluoromethylbenzyl | 33% | 104-106 | 379.5 ES$^-$ (M − H) | 2.63 (s, 3H), 4.06 (s, 3H), 5.37 (s, 2H), 6.71 (d, 1H), 7.48 (d, 1H), 7.56 (d, 2H), 7.69 (d, 2H) |
| 25 | 4-isopropylbenzyl | 37% | 73-75 | 354.9 ES$^+$ (M + H) | 1.25 (s, 3H), 1.27 (s, 3H), 2.62 (s, 3H), 2.93 (m, 1H), 4.05 (s, 3H), 5.38 (s, 2H), 6.79 (d, 1H), 7.20-7.34 (m, 4H), 7.47 (d, 1H) |
| 26 | 4-tertbutylbenzyl | 64% | 82-87 | 369.0 ES$^+$ (M + H) | 1.32 (s, 9H), 2.63 (s, 3H), 4.05 (s, 3H), 5.27 (s, 2H), 6.79 (d, 1H), 7.34 (d, 2H), 7.43 (d, 2H), 7.47 (d, 1H) |
| 27 | 4-phenylbenzyl | 17% | 163-167 | 388.9 ES$^+$ (M + H) | 2.65 (s, 3H), 4.06 (s, 3H), 5.34 (s, 2H), 6.77 (d, 1H), 7.35-7.64 (m, 10H) |
| 28 | 4-methoxybenzyl | 26% | 101-103 | 342.8 ES$^+$ (M + H) | 2.60 (s, 3H), 3.84 (s, 3H), 4.06 (s, 3H), 5.26 (s, 2H), 6.82 (d, 1H), 6.93 (d, 2H), 7.33 (d, 2H), 7.49 (d, 2H), 13.02 (s, 1H) |
| 29 | 4-trifluoromethoxybenzyl | 30% | 130-131 | 396.9 ES$^+$ (M + H) | 2.62 (s, 3H), 4.06 (s, 3H), 5.28 (s, 2H), 6.72 (d, 1H), 7.24 (d, 2H), 7.47 (m, 3H) |
| 30 | 4-benzyloxybenzyl | 35% | 155-157 | 418.8 ES$^+$ (M + H) | 2.59 (s, 3H), 4.05 (s, 3H), 5.08 (s, 2H), 5.24 (s, 2H), 6.80 (d, 1H), 6.99 (d, 2H), 7.30-7.48 (m, 8H) |
| 31 | 4-benzoylbenzyl | 45% | 132-134 | 417.0 ES$^+$ (M + H) | 2.66 (s, 3H), 4.06 (s, 3H), 5.38 (s, 2H), 6.74 (d, 1H), 7.49-7.59 (m, 5H), 7.79-7.87 (m, 4H) |
| 32 | 4-carboxybenzyl | 66% | 183-186 | 356.9 ES$^+$ (M + H) | 2.64 (s, 3H), 4.06 (s, 3H), 5.49 (s, 2H), 6.71 (d, 1H), 7.48 (d, 1H), 7.55 (d, 2H), 8.16 (d, 2H) |

B. 7-Substituted Khellinone Derivatives
The khellinone derivatives which are substituted at the 7 position ($R_5$) were generally synthesised via intermediates 2 or 35 below, which were made from khellin in accordance with the following scheme.
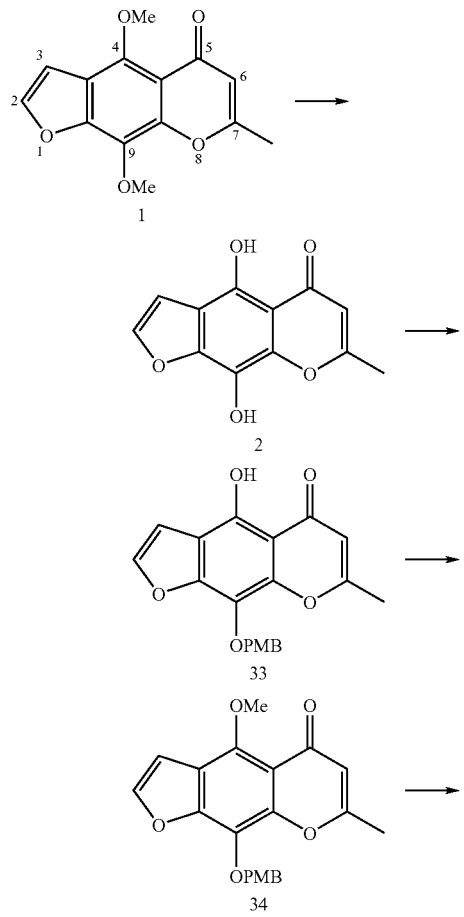
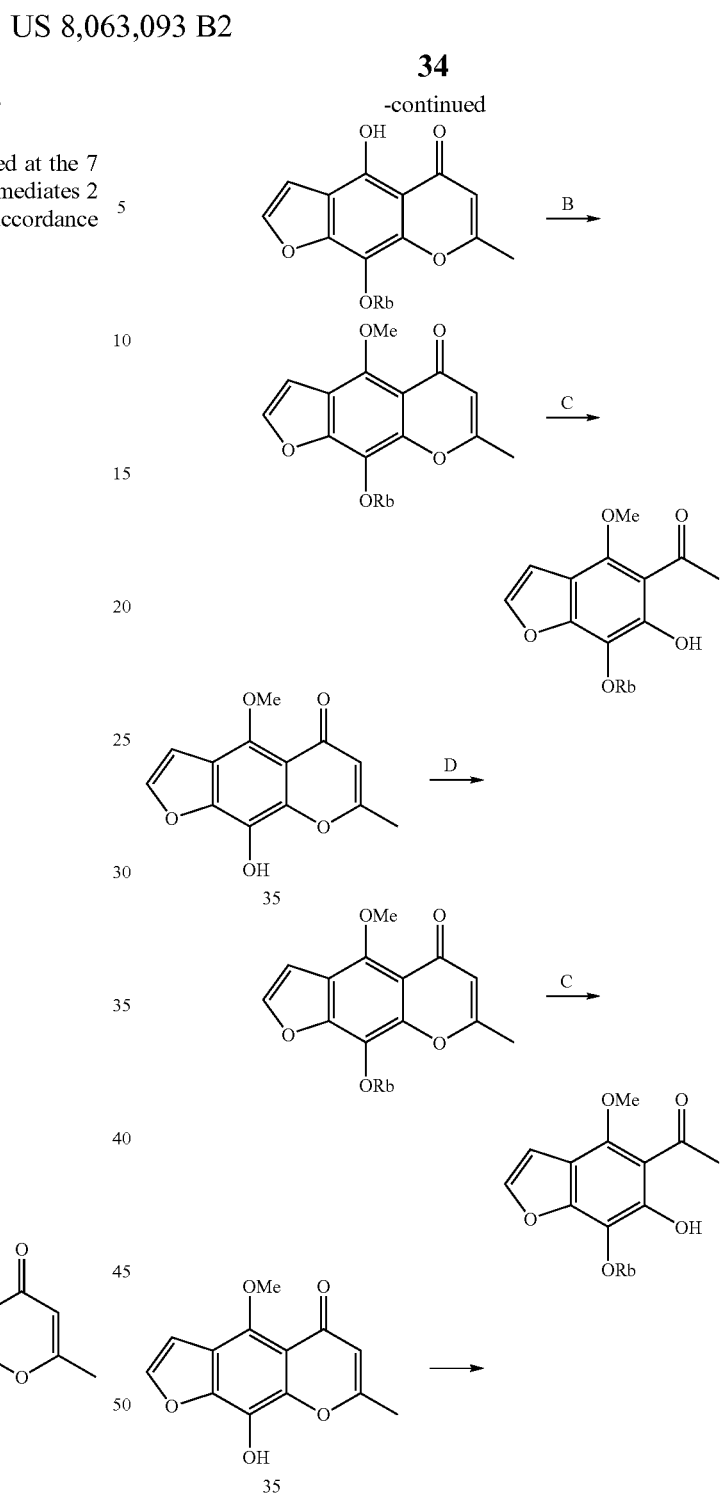
The intermediates 2 and 35 were turned into the compounds of the invention in accordance with the scheme below.
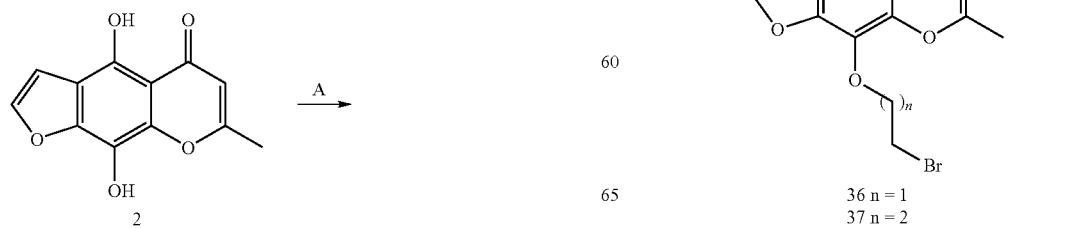

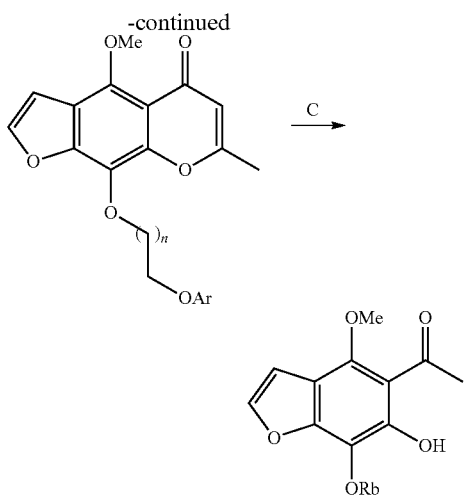

Intermediate 2

4,9-Dihydroxy-7-methyl-furo[3,2-g]chromen-5-one

To a suspension of 1 (10.4 g, 40 mmol) in dichloromethane (100 mL) at −78° C. was added over 75 min boron tribromide (1M in dichloromethane, 80 mL, 80 mmol). The reaction mixture was allowed to warm to rt then was stirred at rt for 16 h. On cooling the reaction mixture to 0° C., the reaction was quenched with water by dropwise addition at first, but at an increasing rate until 50 mL had been added. The reaction mixture was concentrated in vacuo to remove the dichloromethane and the resulting suspension was filtered, washing with water. The orange solid was heated as a suspension in propan-2-ol (200 mL) at 70° C. for 20 min, during which time the solid became pale yellow. The suspension was filtered and the solid was dried to afford 2 (8.4 g, 90%) as a pale yellow solid:

Mp 283-284° C.; $^1$H NMR (d$_6$-DMSO) δ: 2.42 (s, 3H), 6.19 (s, 1H), 7.05 (d, J=2.1 Hz, 1H), 8.02 (d, J=2.1 Hz, 1H), 9.84 (br s, 1H), 12.9 (s, 1H); $^{13}$C NMR (d$_6$-DMSO) δ: 20.2, 104.4, 105.1, 107.0, 112.9, 123.3, 141.8, 145.7, 146.3, 148.2, 168.5, 183.9; MS (ES+) m/z 233 (M+H$^+$).

Intermediate 33

4-hydroxy-9-(4-methoxybenzyl)-7-methyl-furo[3,2-q]chromen-5-one

Compound 2 (1.85 g, 8.0 mmol) was reacted with 4-methoxybenzyl chloride (1.31 mL, 9.6 mmol) according to General Procedure A except that the reaction was quenched with 10% aqueous citric acid. Purification by flash chromatography, eluting with ethyl acetate/petroleum ether (1:4), afforded 33 (2.17 g, 77%) as a colourless solid:

Mp 127-129° C.; $^1$H NMR (CDCl$_3$) δ: 2.31 (s, 3H), 3.75 (s, 3H), 5.15 (s, 2H), 5.96 (s, 1H), 6.83 (d, J=8.7 Hz, 2H), 6.94 (d, J=2.1 Hz, 1H), 7.33 (d, J=8.7 Hz, 2H), 7.57 (d, J=2.1 Hz, 1H); $^{13}$C NMR (d$_6$-DMSO) δ: 20.4, 55.0, 64.6, 75.5, 104.5, 105.3, 113.4, 113.5, 124.4, 128.7, 130.0, 144.8, 145.8, 149.9, 151.3, 159.5, 167.2, 183.9; MS (ES+) m/z 353 (M+H$^+$).

Intermediate 35

4-methoxy-9-hydroxy-7-methyl-furo[3,2-g]chromen-5-one

Compound 33 (1.80 g, 5.1 mmol) was reacted according to General Procedure B to afford the methyl ether 34, which was treated directly with trifluoroacetic acid (15 mL) in dichloromethane (12 mL). The solution was stirred at rt for 2.5 h and then concentrated in vacuo to give a residue that was purified by flash chromatography, eluting with a gradient from ethyl acetate/petroleum ether (3:2) to ethyl acetate, to afford 35 (1.22 g, 97% over two steps) as a colourless solid.

Mp 193-196° C.; $^1$H NMR (CDCl$_3$) δ: 2.32 (s, 3H), 3.82 (s, 3H), 5.99 (s, 1H), 7.10 (d, J=2.4 Hz, 1H), 8.02 (d, J=2.4 Hz, 1H), 10.20 (s, 1H); $^{13}$C NMR (d$_6$-DMSO) δ: 19.5, 61.9, 105.0, 109.8, 113.3, 119.1, 127.7, 143.3 143.5, 145.8, 146.9, 164.3, 177.1; MS (ES+) m/z 247 (M+H$^+$).

Intermediate 36

9-(2-Bromoethoxy)-4-methoxy-7-methyl-furo[3,2-g]chromen-5-one

To a suspension of 35 (500 mg, 2.03 mmol) and K$_2$CO$_3$ (838 mg, 6.06 mmol) in dry DMF (8 mL) was added 1,2-dibromoethane (0.52 mL, 6.06 mmol) and the reaction mixture was stirred at 60° C. for 2 h. The reaction was allowed to cool, quenched with 10% aqueous citric acid (30 mL) and extracted with ethyl acetate (50 mL). The organic layer was washed with water (2×50 mL) and brine (30 mL) and dried over MgSO$_4$. The solvent was removed in vacuo and the crude product was purified by flash chromatography eluting with a gradient from ethyl acetate/dichloromethane (1/9) to (2/9) to give 36 (490 mg, 69%) as a tan solid.

$^1$H-NMR (CDCl$_3$) δ 2.38 (s, 3H), 3.69 (t, J=6.4 Hz, 2H), 4.06 (s, 3H), 4.60 (t, J=6.4 Hz, 2H), 6.04 (s, 1H), 7.01 (d, J=2.2 Hz, 1H), 7.61 (d, J=2.2 Hz, 1H). MS (ES$^+$) m/z 353, 355 (M+H$^+$).

Intermediate 37

4-methoxy-9-(3-bromopropoxy)-7-methyl-furo[3,2-g]chromen-5-one

A suspension of 35 (490 mg, 2.0 mmol), potassium carbonate (330 mg, 2.4 mmol) and 1,3-dibromopropane (2.0 mL, 20 mmol) in anhydrous dimethylformamide (20 mL) was stirred under nitrogen at 60° C. for 5 h. The reaction mixture was then diluted with ethyl acetate (100 mL) and washed with 10% aqueous citric acid (2×50 mL) and brine (50 mL), dried (MgSO$_4$), and concentrated in vacuo. The crude was purified by flash chromatography eluting with a gradient from ethyl acetate/petroleum ether (2:3) to (3:2), to afford 37 (0.50 g, 68%) as a tan solid.

$^1$H NMR (CDCl$_3$) δ: 2.35 (m, 2H), 3.76 (t, 2H), 4.06 (s, 3H), 4.44 (t, 2H), 6.09 (s, 1H), 7.01 (d, J=2.4 Hz, 1H), 7.61 (d, J=2.4 Hz, 1H); MS (ES+) m/z 367, 369 (M+H$^+$).

General Procedure A. Alkylation of di-4,9-(desmethyl)khellin

A suspension of 2 (1.0 equiv.), potassium carbonate (2.0 equiv.) and alkyl or benzyl halide (1.1 equiv.) in anhydrous dimethylformamide (0.25 M) was stirred under nitrogen at 60° C. until completion as determined by TLC (typically 2-4 h). The reaction mixture was then diluted with ethyl acetate and washed with 2M HCl (twice) and brine, dried (MgSO$_4$), and concentrated in vacuo, The crude was purified by flash chromatography.

General Procedure B Methylation of 9-alkyl-4-(desmethyl)khellin

A suspension of the phenol (1.0 equiv.), caesium carbonate (5.0 equiv.) and iodomethane (5.0 equiv.) in anhydrous dimethylformamide (0.15 M) was stirred under nitrogen at rt for 16 h. The reaction mixture was partitioned over 2M HCl and ethyl acetate and the organic phase was extracted with 2M HCl (twice) then washed with brine. After drying (MgSO$_4$) and evaporation the residue was either purified by flash chromatography or used directly in the following step.

General Procedure C Hydrolysis of 4-methyl-9-alkylkhellin

To a solution of the khellin analogue in ethanol (2 parts, 0.01-0.1 M) at reflux was added slowly 3M NaOH or KOH (1 part) and the resulting solution was stirred at reflux for 3-4 h. The reaction mixture was concentrated in vacuo to one third of the original volume and then acidified to pH2 by Universal indicator with 2M HCl. If precipitation occurred, the solid was collected by filtration washing with water. The solid was then dried in the presence of P$_2$O$_5$. If precipitation did not occur the acidified reaction mixture was extracted with ethyl acetate (twice) and the pooled organics were washed with brine, dried (MgSO$_4$) and concentrated in vacuo. The crude product was purified by flash chromatography.

General Procedure D Alkylation of 9-desmethylkhellin

A suspension of 35 (1.0 equiv.), caesium carbonate (2.0 equiv.), potassium iodide (1.0 equiv.) and the chloroalkane (2.0 equiv.) in anhydrous dimethylformamide (0.20 M) was stirred at 60° C. until completion as determined by TLC (typically 2-3 d). The reaction mixture was partitioned over 2M HCl and ethyl acetate and the organic phase was extracted with 2M HCl (twice) then washed with brine. After drying (MgSO$_4$) and evaporation the residue was purified by flash chromatography.

General Procedure E Alkylation of 36 or 37 with phenols/imidazoles

A suspension of alkyl bromide 36 or 37 (1.0 equiv.), Cs$_2$CO$_3$ or K$_2$CO$_3$ (2.5 equiv.) and the phenol/imidazole (1.5-3.0 equiv.) in anhydrous DMF (~1.5 mL/60 mg of bromide) in a screw cap vial was shaken at 60° C. overnight. The reaction was quenched with 10% aqueous citric acid or saturated NH$_4$Cl and extracted with ethyl acetate or dichloromethane. The organic layer was washed twice with water then with brine, dried over MgSO$_4$ and concentrated in vacuo. The crude product was purified by flash chromatography.

The following examples were prepared by the above methods.

TABLE 2

Preparation of 7-substituted khellinones of formula I (X = O, R$_1$ = R$_2$ = H, R$_3$ = Me, R$_4$ = OMe, R$_5$ = ORb)

| Compd | Rb | Yield | Mp °C. | MS | $^1$H NMR (CDCl$_3$) δ: |
|---|---|---|---|---|---|
| 38 | 2-naphthylmethyl | 39% from 2 | 114-115 | 362.8 ES$^+$ (M + H) | 2.70 (s, 3H), 4.11 (s, 3H), 5.41 (s, 2H), 6.84 (d, 1H), 7.43-7.46 (m, 3H), 7.71 (d, 1H), 7.82 (m, 3H), 7.93 (s, 1H) |
| 39 | benzyl | 11% from 2 | 79-80 | 312.9 ES$^+$ (M + H) | 2.73 (s, 3H), 4.14 (s, 3H), 5.26 (s, 2H), 6.87 (d, 1H), 7.27-7.53 (m, 6H), 13.14 (s, 1H) |
| 40 | phenethyl | 32% from 2 | 102-104 | 327.0 ES$^+$ (M + H) | 2.71 (s, 3H), 3.14, (t, 2H), 4.12 (s, 3H), 4.40 (t, 2H), 6.87 (d, 1H), 7.18-7.30 (m, 5H), 7.47 (d, 1H) |
| 41 | 3-(phenyl)propyl | 37% from 2 | 36 | 341.0 ES$^+$ (M + H) | 2.09 (m, 2H), 2.71, (s, 3H), 2.87 (t, 2H), 4.12 (s, 3H), 4.21 (t, 2H), 6.87 (d, 1H), 7.16-7.27 (m, 5H), 7.47 (d, 1H) |
| 42 | 4-(phenyl)butyl | 83% from 35 | 28 | 355.1 ES$^+$ (M + H) | 1.85 (m, 4H), 2.69 (m, 2H), 2.72, (s, 3H), 4.12 (s, 3H), 4.20 (t, 2H), 6.87 (d, 1H), 7.16-7.28 (m, 5H), 7.47 (d, 1H) |
| 43 | 5-(phenyl)pentyl | 28% from 35 | 31-32 | 369.1 ES$^+$ (M + H) | 1.55 (m, 2H), 1.66 (m, 2H), 1.78 (m, 2H), 2.63 (t, 2H), 2.71, (s, 3H), 4.12 (s, 3H), 4.17 (t, 2H), 6.87 (d, 1H), 7.13-7.28 (m, 5H), 7.46 (d, 1H) |
| 44 | 2-fluorobenzyl | 12% from 2 | 89-92 | 330.9 ES$^+$ (M + H) | 2.71 (s, 3H), 4.13 (s, 3H), 5.31 (s, 2H), 6.86 (d, 1H), 7.05 (dd, 1H), 7.12 (dd, 1H), 7.27 (m, 1H), 7.45 (d, 1H), 7.65 (dd, 1H) |
| 45 | 2-chlorobenzyl | 11% from 2 | 104-107 | 346.9 ES$^+$ (M + H) | No data |
| 46 | 2-methylbenzyl | 31% from 2 | 86-88 | 326.8 ES$^+$ (M + H) | 2.49 (s, 3H), 2.71 (s, 3H), 4.12 (s, 3H), 5.24 (s, 2H), 6.85 (d, 1H), 7.18 (m, 3H), 7.45-7.53 (d, 2H) |
| 47 | 2-phenylbenzyl | 35% from 2 | 115-117 | 388.9 ES$^+$ (M + H) | 2.70 (s, 3H), 4.11 (s, 3H), 5.12 (s, 2H), 6.83 (d, 1H), 7.30-7.49 (m, 9H), 7.78 (m, 1H) |
| 48 | 3-fluorobenzyl | 33% from 2 | 89-91 | 330.9 ES$^+$ (M + H) | 2.71 (s, 3H), 4.12 (s, 3H), 5.22 (s, 2H), 6.86 (d, 1H), 6.96 (m, 1H), 7.24-7.30 (m, 3H), 7.47 (d, 1H) |
| 49 | 3-chlorobenzyl | 40% from 2 | 105-108 | 346.9 ES$^+$ (M + H) | 2.71 (s, 3H), 4.13 (s, 3H), 5.24 (s, 2H), 6.86 (d, 1H), 7.25 (m, 2H), 7.39 (m, 1H), 7.47 (d, 1H), 7.54 (m, 1H) |
| 50 | 3-methylbenzyl | 29% from 2 | 81-82 | 326.8 ES$^+$ (M + H) | 2.34 (s, 3H), 2.71 (s, 3H), 4.12 (s, 3H), 5.19 (s, 2H), 6.86 (d, 1H), 7.09 (d, 1H), 7.22 (m, 1H), 7.32 (m, 2H), 7.47 (d, 1H) |
| 51 | 3-carboxybenzyl | 42% from 2 | 192-195 | 356.3 ES$^+$ (M + H) | 2.71 (s, 3H). 4.13 (s, 3H), 5.29 (s, 2H), 6.89 (d, 1H), 4.47 (m, 3H), 7.83 (d, 1H), 8.03 (d, 1H), 8.22 (s, 1H) |

TABLE 2-continued

Preparation of 7-substituted khellinones of formula I (X = O, $R_1 = R_2 = H$, $R_3 = Me$, $R_4 = OMe$, $R_5 = ORb$)

| Compd | Rb | Yield | Mp °C. | MS | $^1$H NMR (CDCl$_3$) δ: |
|---|---|---|---|---|---|
| 52 | 3-nitrobenzyl | 10% from 2 | 157-159 | 356.3 ES$^-$ (M − H) | 2.71 (s, 3H), 4.14 (s, 3H), 5.39 (s, 2H), 6.88 (d, 1H), 7.50 (m, 2H), 7.88 (d, 1H), 8.14 (d, 1H), 8.39 (s, 1H) |
| 53 | 4-fluorobenzyl | 46% from 2 | 99-100 | 330.9 ES$^+$ (M + H) | 2.70 (s, 3H), 4.11 (s, 3H), 5.18 (s, 2H), 6.85 (d, 1H), 7.00 (m, 2H), 7.45 (m, 3H) |
| 54 | 4-chlorobenzyl | 18% from 2 | 110 | 346.8 ES$^+$ (M + H) | 2.71 (s, 3H), 4.12 (s, 3H), 5.19 (s, 2H), 6.86 (d, 1H), 7.28 (d, 2H), 7.45 (m, 3H) |
| 55 | 4-bromobenzyl | 31% from 2 | 106-107 | 390.8 392.8 ES$^+$ (M + H) | 2.70 (s, 3H), 4.12 (s, 3H), 5.18 (s, 2H), 6.86 (d, 1H), 7.37-7.46 (m, 5H) |
| 56 | 4-trifluoromethyl benzyl | 35% from 2 | 90-91 | 381.2 ES$^+$ (M + H) | 2.71 (s, 3H), 4.13 (s, 3H), 5.28 (s, 2H), 6.87 (d, 1H), 7.46 (d, 1H), 7.61 (m, 4H) |
| 57 | 4-isopropyl benzyl | 50% from 2 | 80-83 | 354.9 ES$^+$ (M + H) | 1.24 (m, 6H), 2.71 (s, 3H), 2.89 (m, 1H), 4.11 (s, 3H), 5.19 (s, 2H), 6.85 (d, 1H), 7.20 (d, 2H), 7.45 (m, 3H) |
| 58 | 4-tertbutylbenzyl | 40% from 2 | 117-118 | 368.9 ES$^+$ (M + H) | 1.30 (s, 9H), 2.71 (s, 3H), 4.12 (s, 3H), 5.19 (s, 2H), 6.85 (d, 1H), 7.36 (d, 2H), 7.45 (m, 3H) |
| 59 | 4-phenylbenzyl | 12% from 2 | 126-127 | 388.9 ES$^+$ (M + H) | 2.72 (s, 3H), 4.12 (s, 3H), 5.28 (s, 2H), 6.86 (d, 1H), 7.30-7.61 (m, 10H) |
| 60 | 4-trifluoro methoxybenzyl | 58% from 2 | 86-88 | 357.4 ES$^+$ (M + H) | 2.70 (s, 3H), 4.12 (s, 3H), 5.21 (s, 2H), 6.86 (d, 1H), 7.17 (d, 2H), 7.45 (d, 1H), 7.55 (d, 2H) |
| 61 | 4-benzyloxy benzyl | 6% from 2 | 118-120 | 418.7 ES$^+$ (M + H) | 2.71 (s, 3H), 4.11 (s, 3H), 5.06 (s, 2H), 5.16 (s, 2H), 6.84 (d, 1H), 6.92 (d, 2H), 7.24-7.45 (m, 8H) |
| 62 | 4-benzoylbenzyl | 11% from 2 | 144-145 | 416.4 ES$^+$ (M + H) | 2.71 (s, 3H), 4.13 (s, 3H), 5.32 (s, 2H), 6.88 (d, 1H), 7.43-7.66 (m, 5H), 7.75-7.79 (m, 4H) |
| 63 | 4-carboxybenzyl | 53% from 2 | 208-209 | 355.3 ES$^-$ (M − H) | 2.60 (s, 3H), 4.08 (s, 3H), 5.21 (s, 2H), 7.23 (d, 1H), 7.62 (d, 2H), 7.90 (m, 3H) |
| 64 | phenoxyethyl | 33% from 2 | — | 343.2 ES$^+$ (M + H) | 2.71 (s, 3H), 4.13 (s, 3H), 4.31 (t, 2H), 4.54 (t, 2H), 6.87 (m, 4H), 7.27 (m, 2H), 7.43 (d, 1H) |
| 65 | 4-chlorophenoxy ethyl | 54% from 2 | — | 377.1 ES$^+$ (M + H) | 2.70 (s, 3H), 4.13 (s, 3H), 4.27 (t, 2H), 4.51 (t, 2H), 6.85 (m, 3H), 7.18 (m, 2H), 7.43 (d, 2H) |
| 66 | 5-bromo-2,4,-difluorophenoxy ethyl | 24% from 2 | — | 457, 459 ES$^+$ (M + H) | 2.70 (s, 3H), 4.13 (s, 3H), 4.39 (t, 2H), 4.55 (t, 2H), 6.81 (m, 1H), 6.87 (d, 1H), 7.05 (m, 1H), 7.47 (d, 1H) |
| 67 | 4-carbamoyl phenoxyethyl | 32% from 36 | — | 385.9 ES$^+$ (M + H) | 2.71 (s, 3H), 4.14 (s, 3H), 4.36 (t, 2H), 4.55 (t, 2H), 5.70 (br s, 2H), 6.87 (d, 1H), 6.93 (d, 2H), 7.43 (d, 1H), 7.74 (d, 2H), 13.13 (s, 1H) |
| 68 | 2,3,5,6-tetrafluoro phenoxyethyl | 32% from 36 | — | 414.8 ES$^+$ (M + H) | 2.71 (s, 3H), 4.13 (s, 3H), 4.51-4.54 (m, 2H), 4.57-4.60 (m, 2H), 6.73 (m$_c$, 1H), 6.87 (d, 1H), 7.45 (d, 1H), 13.09 (s, 1H) |
| 69 | 2-methyl phenoxyethyl | 12% from 36 | — | 356.9 ES$^+$ (M + H) | 2.11 (s, 3H), 2.71 (s, 3H), 4.12 (s, 3H), 4.32 (t, 2H), 4.57 (t, 2H), 6.80-6.83 (m, 2H), 6.86 (d, 1H), 7.07-7.13 (m, 2H), 7.43 (d, 1H), 13.06 (s, 1H) |
| 70 | 3-methyl phenoxyethyl | 20% from 36 | — | 356.9 ES$^+$ (M + H) | 2.30 (s, 3H), 2.71 (s, 3H), 4.13 (s, 3H), 4.30 (t, 2H), 4.53 (t, 2H), 6.68-6.75 (m, 3H), 6.86 (d, 1H), 7.12 (t, 1H), 7.44 (d, 1H), 13.05 (s, 1H) |
| 71 | 4-methyl phenoxyethyl | 41% from 36 | — | 356.9 ES$^+$ (M + H) | 2.26 (s, 3H), 2.71 (s, 3H), 4.13 (s, 3H), 4.28 (t, 2H), 4.52 (t, 2H), 6.79 (d, 2H), 6.86 (d, 1H), 7.04 (d, 2H), 7.45 (d, 1H), 13.04 (s, 1H) |
| 72 | 2-fluoro phenoxyethyl | 42% from 36 | — | 360.9 ES$^+$ (M + H) | 2.71 (s, 3H), 4.13 (s, 3H), 4.39 (t, 2H), 4.56 (t, 2H), 6.84-6.91 (m, 2H), 7.00-7.10 (m, 3H), 7.45 (d, 1H), 13.11 (s, 1H) |
| 73 | 4-fluoro phenoxyethyl | 18% from 36 | — | 360.9 ES$^+$ (M + H) | 2.71 (s, 3H), 4.13 (s, 3H), 4.27 (m$_c$, 2H), 4.51 (m$_c$, 2H), 6.81-6.96 (m, 5H), 7.44 (t, 1H), 13.12 (s, 1H) |
| 74 | 1-naphthyloxy ethyl | 30% from 36 | — | 392.9 ES$^+$ (M + H) | 2.70 (s, 3H), 4.10 (s, 3H), 4.50 (t, 2H), 4.71 (t, 2H), 6.79-6.81 (m, 2H), 7.28-7.46 (m, 5H), 7.74 (d, 1H), 8.03 (d, 1H), 13.13 (s, 1H) |

TABLE 2-continued

Preparation of 7-substituted khellinones of formula I (X = O, $R_1 = R_2 = H, R_3 = Me, R_4 = OMe, R_5 = ORb$)

| Compd | Rb | Yield | Mp °C. | MS | $^1$H NMR (CDCl$_3$) δ: |
|---|---|---|---|---|---|
| 75 | 2-naphthyloxy ethyl | 37% from 36 | — | 392.9 ES$^+$ (M + H) | 2.71 (s, 3H), 4.13 (s, 3H), 4.43 (t, 2H), 4.61 (t, 2H), 6.86 (d, 1H), 7.11-7.14 (m, 2H), 7.31 (t, 1H), 7.38-7.43 (m, 2H), 7.68-7.75 (m, 3H), 13.11 (s, 1H) |
| 76 | 2-pyridyloxy ethyl | 15% from 36 | — | 343.9 ES$^+$ (M + H) | 2.69 (s, 3H), 4.11 (s, 3H), 4.34 (m, 2H), 4.46 (m, 2H), 6.17 (t, 1H), 6.56 (d, 1H), 6.85 (s, 1H), 7.32-7.39 (m, 2H), 7.69 (d, 1H), 13.08 (s, 1H) |
| 77 | 3-pyridyloxy ethyl | 21% from 36 | — | 343.9 ES$^+$ (M + H) | 2.71 (s, 3H), 4.13 (s, 3H), 4.36 (t, J = 4.7 Hz, 2H), 4.55 (t, J = 4.7 Hz, 2H), 6.87 (d, J = 2.3 Hz, 1H), 7.16-7.23 (m, 2H), 7.43 (d, J = 2.3 Hz, 1H), 8.19 (dd, J = 1.4, 4.2 Hz, 1H), 8.27 (d, J = 2.4 Hz, 1H), 13.14 (s, 1H) |
| 78 | 4-pyridyloxy ethyl | 11% from 36 | — | 343.9 ES$^+$ (M + H) | 2.71 (s, 3H), 4.14 (s, 3H), 4.36 (m$_c$, 2H), 4.55 (m$_c$, 2H), 6.80 (d, 2H), 6.87 (d, 1H), 7.42 (d, 1H), 8.40 (br s, 2H) |
| 79 | 1-imidazolyl ethyl | 19% from 36 | — | 316.9 ES$^+$ (M + H) | 2.71 (s, 3H), 4.13 (s, 3H), 4.33 (t, 2H), 4.44 (t, 2H), 6.87 (d, 1H), 7.11 (br s, 2H), 7.46 (d, 1H), 7.72 (br s, 1H), 13.20 (s, 1H) |
| 80 | phenoxypropyl | 43% from 37 | — | 357.2 ES$^+$ (M + H) | 2.23 (m, 2H), 2.70 (s, 3H), 4.11 (s, 3H), 4.26 (t, 2H), 4.37 (t, 2H), 6.84 (d, 1H), 6.92 (m, 3H), 7.25 (m, 2H), 7.38 (d, 2H) |
| 81 | 3-(1-benzimidazolyl) propyl | 54% from 37 | — | 380.9 ES$^+$ (M + H) | 2.28 (quintet, 2H), 2.72 (s, 3H), 4.12 (t, 2H), 4.14 (s, 3H), 4.59 (t, 2H), 6.89 (d, 1H), 7.23-7.30 (m, 2H), 7.46-7.48 (m, 1H), 7.48 (d, 1H), 7.77-7.80 (m, 1H), 8.09 (s, 1H), 13.25 (s, 1H) |

*$^1$H NMR (d$_6$-DMSO)

C. 4,7-disubstituted khellinone derivatives

The khellinone derivatives which are substituted at the 4 and 7 position ($R_4$ and $R_5$) synthesised via intermediate 2, which has been described previously, in accordance with the following scheme.

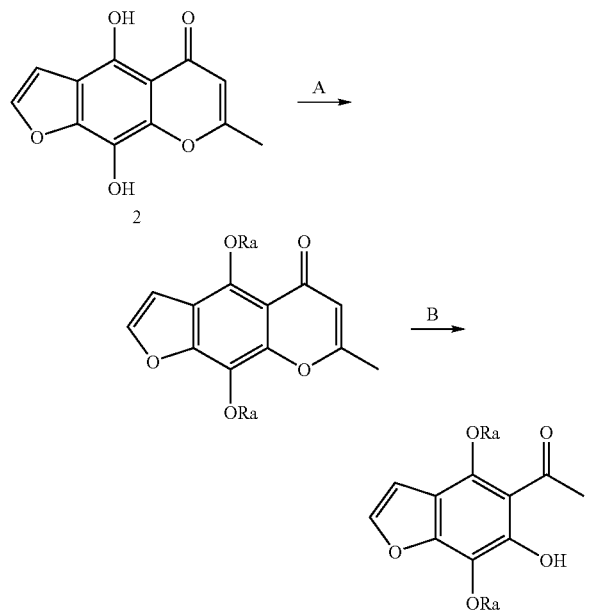

General Procedure A Dialkylation of Intermediate 2

A suspension of 2 (1.0 equiv.), caesium carbonate (3.0 equiv.) and alkyl halide (3.0 equiv. or 1.1 equiv. for preparation of compound 84) was stirred at 60° C. for 3 h, then diluted with ethyl acetate (30 mL) and washed with 2M HCl (3×15 mL) and brine (15 mL). This solution was dried over MgSO$_4$ and concentrated in vacuo to give a residue that was purified by flash chromatography.

General Procedure B Hydrolysis of 4,9-dialkylkhellin

To a solution of the khellin analogue in ethanol (2 parts, 0.01-0.1 M) at reflux was added slowly 3M NaOH or KOH (1 part) and the resulting solution was stirred at 90° C. for 3 h. The reaction was allowed to cool and quenched with 10% aqueous citric acid and extracted with ethyl acetate. The organic layer was washed with brine, dried over MgSO$_4$ and concentrated in vacuo. The crude product was purified by flash chromatography.

The following examples were prepared by the above method.

TABLE 3

Preparation of 4,7-disubstituted khellinones of formula I (X = O, $R_1 = R_2 = H$, $R_3 = Me$, $R_4 = R_5 = ORa$)

| Compd | Ra | Yield from 2 | Mp °C. | MS | $^1$H NMR (CDCl$_3$) δ: |
|---|---|---|---|---|---|
| 82 | benzyl | 35% | 74-76 | 389.3 ES$^+$ (M + H) | 2.60 (s, 3H), 5.26 (s, 2H), 5.30 (s, 2H), 6.75 (d, J = 2.3 Hz, 1H), 7.25-7.78 (m, 11H) |
| 83 | 3-(phenyl)propyl | 8% | — | 445.0 ES$^+$ (M + H) | 2.03-2.25 (m, 4H), 2.75 (s, 3H), 2.85 (q, J = 7.6, 4H), 4.20 (t, J = 6.3, 2H), 4.32 (t, J = 6.3, 2H), 6.70 (d, J = 2.1, 1H), 7.14-7.33 (m, 10H), 7.42 (d, J = 2.1, 1H), 13.05 (s, 1H, OH) |

D. Dimers

The khellinone dimers which were linked at the 4 positions ($R_4$) were generally synthesised in accordance with the following general reaction scheme.

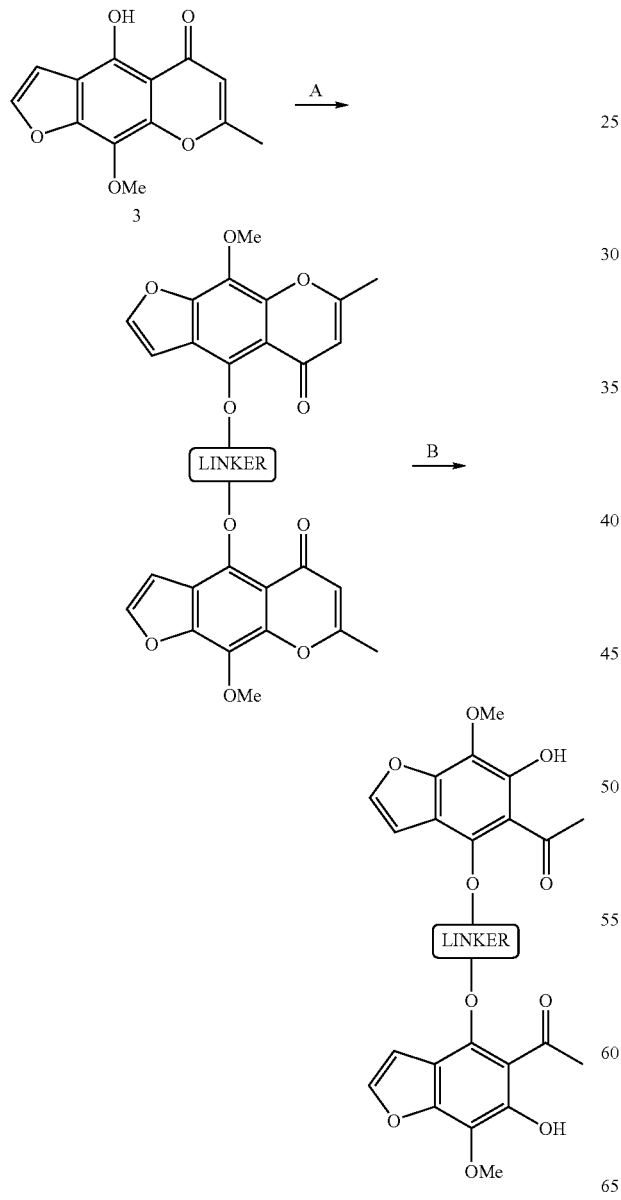

General Procedure A Linkage of 4-desmethyllkhellin

A suspension of 3 (1.0 mmol), caesium carbonate (2.0 mmol) and diiodoalkane (or α,α'-dibromoxylene) (0.5 mmol) in anhydrous dimethylacetamide (10 mL) was stirred under nitrogen at 60° C. until completion as determined by TLC (typically 24 h). The reaction mixture was then diluted with ethyl acetate and washed with 2M HCl (twice) and brine, dried (MgSO$_4$), and concentrated in vacuo. The crude was purified by flash chromatography.

General Procedure B Hydrolysis of 4,4-linked dikhellin

To a solution of the khellin analogue in ethanol (2 parts, 0.01-0.1 M) at reflux was added slowly 3M NaOH (1 part) and the resulting solution was stirred at reflux for 3 h. The reaction mixture was concentrated in vacuo to one third of the original volume and then acidified to pH2 by Universal indicator with 2M HCl. If precipitation occurred, the solid was collected by filtration washing with water. The solid was then dried in the presence of P$_2$O$_5$. If precipitation did not occur the acidified reaction mixture was extracted with ethyl acetate (twice) and the pooled organics were washed with brine, dried (MgSO$_4$) and concentrated in vacuo.

The following examples were prepared by the above method.

TABLE 4

Preparation of 4-4 substituted khellinone dimers of the formula IV

Formula IV

| Compd | Linker | Yield | Mp | MS | $^1$H |
|---|---|---|---|---|---|
| 84 | —(CH$_2$)$_n$—, n = 4 | 25% | 209-211 | 498.9 ES$^+$ (M + H) | 2.12 (m, 4H), 2.72 (s, 6H), 4.04 (s, 6H), 4.38 (m, 4H), 6.80 (d, 2H), 7.49 (d, 2H) |
| 85 | —(CH$_2$)$_n$—, n = 5 | 44% | 139-141 | 513.0 ES$^+$ (M + H) | 1.74 (m, 2H), 1.95 (m, 6H), 2.71 (s, 6H), 4.04 (s, 6H), 4.33 (t, 4H), 6.80 (d, 2H), 7.47 (d, 2H) |
| 86 | —(CH$_2$)$_n$—, n = 6 | 51% | 147-151 | 527.1 ES$^+$ (M + H) | 1.60, (m, 4H), 1.91 (m, 4H), 2.73 (s, 6H), 4.03 (s, 6H), 4.31 (m, 4H), 6.80 (d, 2H), 7.47 (d, 2H) |
| 87 | —(CH$_2$)$_n$—, n = 7 | 37% | 122-125 | 541.1 ES$^+$ (M + H) | 1.52 (m, 6H), 1.86 (m, 4H), 2.72 (s, 6H), 4.02 (s, 6H), 4.29 (t, 4H), 6.81 (d, 2H), 7.46 (d, 2H) |
| 88 | m-xylyl | 26% | 184-186 | 546.9 ES$^+$ (M + H) | 2.61 (s, 6H), 4.05 (s, 6H), 5.30 (s, 4H), 6.73 (d, 2H), 7.43 (m, 4H), 7.47 (d, 2H) |
| 89 | p-xylyl | 16% | 201-203 | 546.8 ES$^+$ (M + H) | 2.61 (s, 6H), 4.05 (s, 6H), 5.28 (s, 4H), 6.78 (d, 2H), 7.46 (d, 2H), 7.57 (m, 4H) |

The khellinone dimers which were linked at the 7 positions (R5) were generally synthesised in accordance with the following general reaction scheme. The syntheses of intermediates 2 and 35 are described above.

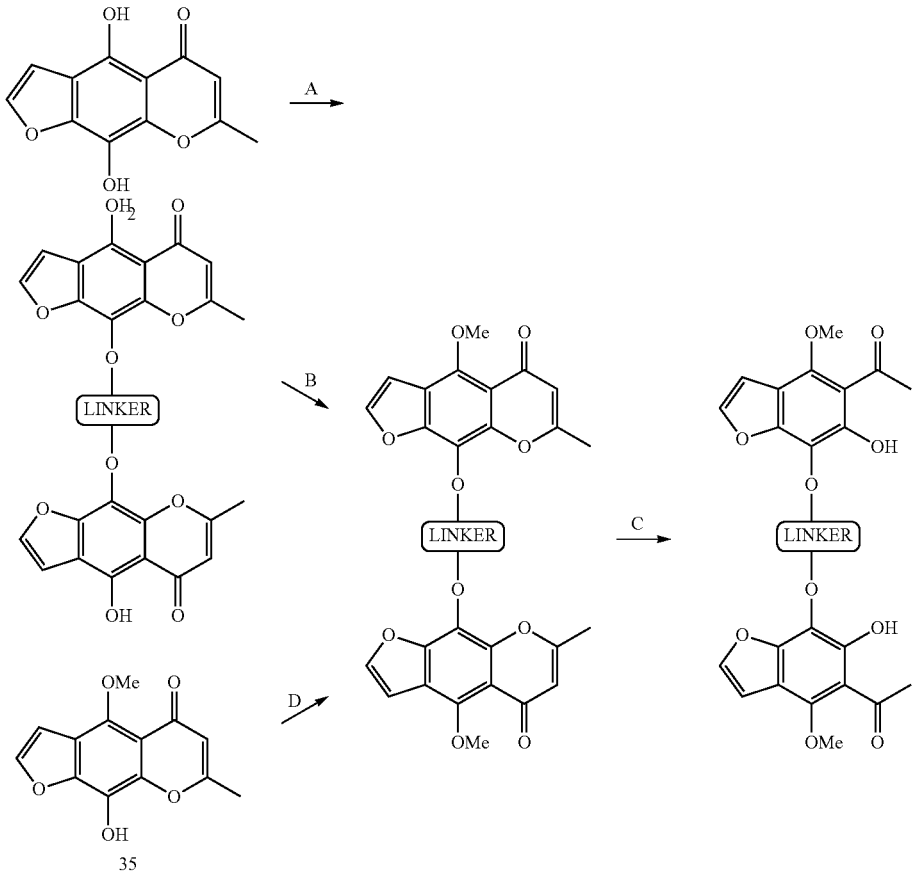

General Procedure A Alkylation of di-4,7-(desmethyl)khellin

A suspension of 2 (1.0 mmol), potassium carbonate (1.5 mmol) and dihalide (0.5 mmol) in anhydrous acetonitrile (0.25 M) was stirred under nitrogen at reflux until completion as determined by TLC (typically 20 h). The reaction mixture was then diluted with ethyl acetate and washed with 2M HCl (twice) and brine, dried (MgSO$_4$), and concentrated in vacuo. The crude was purified by flash chromatography.

General Procedure B Dimethylation of 7-linked 4-(desmethyl)khellin dimer

A suspension of the diphenol (1.0 equiv.), caesium carbonate (10.0 equiv.) and iodomethane (5.0 equiv.) in anhydrous dimethylacetamide (0.05-0.2 M) was stirred under nitrogen at rt for 4 h to 2 d. The reaction mixture was partitioned over 2M HCl and ethyl acetate and the organic phase was extracted with 2M HCl (twice) then washed with brine. After drying (MgSO$_4$) and evaporation the residue was either purified by flash chromatography or used directly in the following step.

General Procedure C Hydrolysis of 7-linked khellin dimer

To a solution of the khellin analogue in ethanol (2 parts, 0.01-0.1 M) at reflux was added slowly 3M NaOH (1 part) and the resulting solution was stirred at reflux for 3 h. The reaction mixture was concentrated in vacuo to one third of the original volume and then acidified to pH2 by Universal indicator with 2M HCl. If precipitation occurred, the solid was collected by filtration washing with water. The solid was then dried in the presence of P$_2$O$_5$. If precipitation did not occur the acidified reaction mixture was extracted with ethyl acetate (twice) and the pooled organics were washed with brine, dried (MgSO$_4$) and concentrated in vacuo.

General Procedure D Alkylation of 7-desmethylkhellin

A suspension of 35 (0.75 mmol), potassium carbonate (1.50 mmol), and the dibromoalkane (0.38 mmol) in anhydrous dimethylformamide (0.20 M) was stirred at 60° C. for 1 h then rt for 16 h. The reaction mixture was partitioned over 2M HCl and chloroform and the organic phase was extracted with 2M HCl (twice) then washed with brine. After drying (Na$_2$SO$_4$) and evaporation the residue was purified by flash chromatography.

The following examples were prepared by the above method.

TABLE 5

Preparation of 7-7 substituted khellinone dimers of the formula V

Formula V

| Compd | Linker | Yield | Mp | MS | $^1$H |
|---|---|---|---|---|---|
| 90 | —(CH$_2$)$_n$—, n = 4 | 48% from 35 | 191-193 | 499.3 ES$^+$ (M + H) | 2.02 (m, 4H), 2.67 (s, 6H), 4.12 (s, 6H), 4.27 (m, 4H), 6.86 (m, 2H), 7.47 (d, 2H) |
| 91 | —(CH$_2$)$_n$—, n = 5 | 65% from 35 | 132-134 | 513.4 ES$^+$ (M + H) | 1.72 (m, 2H), 1.88 (m, 4H), 2.69 (s, 6H), 4.11 (s, 6H), 4.24 (t, 4H), 6.85 (d, 2H), 7.46 (d, 2H) |
| 92 | —(CH$_2$)$_n$—, n = 6 | 67% from 35 | 109-111 | 527.5 ES$^+$ (M + H) | 1.55 (m, 4H), 1.80 (m, 4H), 2.69 (s, 6H), 4.11 (s, 6H), 4.17 (t, 4H), 6.85 (d, 2H), 7.47 (d, 2H) |
| 93 | —(CH$_2$)$_n$—, n = 7 | 90% from 2 | N/A | 541.4 ES$^+$ (M + H) | 1.41-1.54 (m, 6H), 1.76 (m, 4H), 2.70 (s, 6H), 4.11 (s, 6H), 4.19 (t, 4H), 6.86 (d, 2H), 7.48 (d, 2H) |
| 94 | m-xylyl | 9% from 2 | 125-128 | 547.3 ES$^+$ (M + H) | 2.71 (s, 6H), 4.12 (s, 6H), 5.23 (s, 6H), 6.85 (d, 2H), 7.33 (m, 1H), 7.46 (m, 4H), 7.66 (s, 1H), 13.12 (s, 1H) |
| 95 | p-xylyl | 15% from 2 | 184-186 | 547.3 ES$^+$ (M + H) | 2.70 (s, 6H), 4.12 (s, 6H), 5.23 (s, 6H), 6.85 (d, 2H), 7.45 (d, 2H), 7.48 (m, 4H) |

Compounds 90-92 were prepared from 35 over two steps and compounds 93-95 were prepared from 2 over three steps.

Preparation of 7-6 substituted dimers

The mixed khellinone dimer 98 corresponding to a khellinone substituted at the 7 position where R5 is a hexyl chain substituted with 6-khellinone was prepared as follows. Other mixed dimers may be made using this methodology.

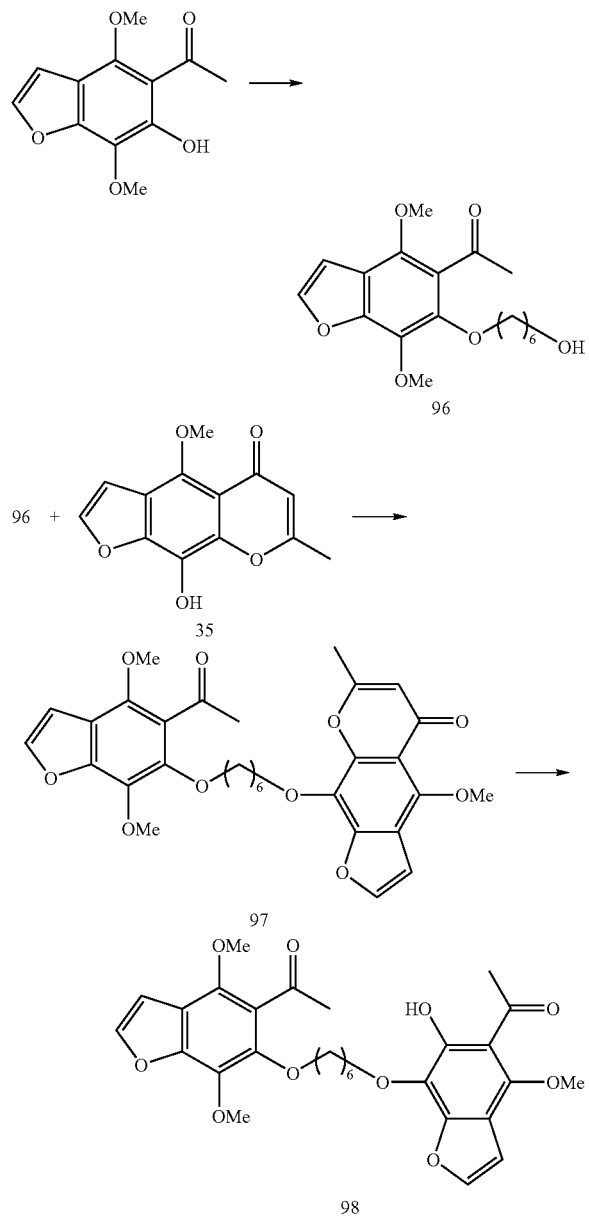

Intermediate 96

A suspension of khellinone (236 mg, 1.0 mmol), 6-bromohexan-1-ol (197 μL, 1.5 mmol) and caesium carbonate (489 mg, 1.5 mmol) in dimethylformamide (5 mL) was stirred at 60° C. for 2 h. The reaction mixture was diluted with ethyl acetate (30 mL) and washed with 2M HCl (3×15 mL) and brine (15 mL), then dried with $MgSO_4$ and concentrated in vacuo. Purification by flash chromatography, eluting with ethyl acetate/petroleum ether (1:2), afforded 96 (248 mg, 85%) as a colourless oil:

$^1$H NMR (CDCl$_3$) δ: 1.40 (m, 4H), 1.57 (m, 2H), 1.72 (m, 2H), 2.51 (s, 3H), 3.65 (t, J=6.3 Hz, 2H), 3.94 (s, 3H), 4.05 (m, 5H), 6.85 (d, J=2.2 Hz, 1H), 7.55 (d, J=2.2 Hz, 1H).

Example 98

To a solution of 96 (140 mg, 0.42 mmol) in dichloromethane (3 mL) was added 35 (102 mg, 0.42 mmol) and triphenylphosphine (120 mg, 0.46 mmol) and the reaction mixture was cooled to 0° C. DEAD (72 μL, 0.46 mmol) was added and the reaction mixture was stirred at 0° C. for 10 min then at rt for 16 h. The reaction mixture was concentrated in vacuo. Purification by flash chromatography, eluting with ethyl acetate/petroleum ether (1:2), afforded a mixture of 97 and triphenylphosphine oxide, which was dissolved in refluxing ethanol (5 mL) and treated with 3M NaOH (5 mL). The reaction mixture was stirred at 90° C. for 2 h then concentrated in vacuo to one third of the original volume and then acidified to pH2 by Universal indicator with 2M HCl. The acidified reaction mixture was extracted with ethyl acetate (twice) and the pooled organics were washed with brine, dried (MgSO$_4$) and concentrated in vacuo. Purification by flash chromatography, eluting with ethyl acetate/petroleum ether (1:4), afforded 98 (46 mg, 20% over two steps) as a yellow oil:

$^1$H NMR (CDCl$_3$) δ: 1.51-1.59 (m, 4H), 1.73-1.84 (m, 2H), 2.51 (s, 3H), 2.71 (s, 3H), 3.97 (s, 3H), 4.05 (m, 5H), 4.12 (s, 3H), 4.19 (t, J=6.7 Hz, 2H), 6.85 (d, J=2.3 Hz, 1H), 6.88 (d, J=2.3 Hz, 1H), 7.49 (d, J=2.3 Hz, 1H), 7.56 (d, J=2.3 Hz, 1H); MS (ES+) m/z 541.3 (M+H$^+$).

General Procedure E 4-substituted khellin derivatives

The khellin derivatives which are substituted at the 4 position (R$_4$) were synthesised as intermediates for the compounds described in Section A The following examples were prepared by the above methods.

TABLE 6

Preparation of 4-substituted khellins of formula VI (X = O, R$_1$ = R$_2$ = H, R$_4$ = ORa, R$_5$ = OMe)

| Compd | Ra | Yield from 3 | Mp °C. | MS | $^1$H NMR (CDCl$_3$) δ: |
|---|---|---|---|---|---|
| 99 | 4-(phenyl)butyl | 57% | 121-122 | 379.2 ES$^+$ (M + H) | 1.83-1.94 (m, 4H), 2.36 (s, 3H), 2.69 (t, 2H), 4.14 (t, 2H), 4.17 (s, 3H), 6.02 (s, 1H), 6.88 (d, 1H), 7.12-7.28 (m, 5H), 7.57 (d, 1H) |

TABLE 6-continued

Preparation of 4-substituted khellins of formula VI (X = O, $R_1 = R_2 = H$, $R_4 = ORa$, $R_5 = OMe$)

| Compd | Ra | Yield from 3 | Mp °C. | MS | $^1$H NMR (CDCl$_3$) δ: |
|---|---|---|---|---|---|
| 100 | 5-(phenyl)butyl | 68% | — | 393.2 ES$^+$ (M + H) | 1.57 (m, 2H), 1.71 (m, 2H), 1.87 (m, 2H), 2.37 (s, 3H), 2.64 (t, 2H). 4.12 (t, 2H), 4.18 (s, 3H), 6.02 (s, 1H), 6.88 (d, 1H), 7.12-7.28 (m, 5H), 7.58 (d, 1H) |

General Procedure F 7-substituted khellin derivatives

The khellin derivatives which are substituted at the 7 position ($R_5$) were synthesised as intermediates for the compounds described in Section B The following examples were prepared by the above methods.

TABLE 7

Preparation of 7-substituted khellin of formula VI (X = O, $R_1 = R_2 = H$, $R_4 = OMe$, $R_5 = ORb$)

| Compd | Rb | Yield | Mp °C. | MS | $^1$H NMR (CDCl$_3$) δ: |
|---|---|---|---|---|---|
| 101 | 3-(phenyl)propyl | 64% from 35 | — | 365.3 ES$^+$ (M + H) | 2.14 (m, 2H), 2.36 (s, 3H), 2.91 (t, 2H). 4.09 (s, 3H), 4.35 (t, 2H), 6.11 (s, 1H), 6.99 (d, 1H), 7.00-7.31 (m, 5H), 7.60 (d, 1H) |
| 102 | 4-(phenyl)butyl | 83% from 35 | — | 379.3 ES$^+$ (M + H) | 1.87 (m, 2H), 2.33 (m, 2H), 2.33 (s, 3H), 2.71 (t, 2H), 4.05 (s, 3H), 4.34 (t, 2H), 6.16 (s, 1H), 7.00 (d, 1H), 7.18 (m, 3H), 7.26 (m, 2H), 7.60 (d, 1H) |
| 103 | 5-(phenyl)butyl | 54% from 35 | — | 393.2 ES$^+$ (M + H) | 1.60 (m, 2H), 1.72 (m, 2H), 1.86 (m, 2H), 2.35 (s, 3H), 2.65 (t, 2H). 4.05 (s, 3H), 4.32 (t, 2H), 6.18 (s, 1H), 7.00 (d, 1H), 7.17 (m, 3H), 7.28 (m, 2H), 7.60 (d, 1H) |
| 104 | 2-fluorophenoxy ethyl | 67% from 36 | — | 384.9 ES$^+$ (M + H) | 2.26 (s, 3H), 4.02 (s, 3H), 4.41-4.44 (m, 2H), 4.68-4.71 (m, 2H), 6.01 (s, 1H), 6.86-6.93 (m, 1H), 6.96-7.07 (m, 4H), 7.58 (d, 1H) |
| 105 | 4-methylphenoxy ethyl | 65% from 36 | — | 380.9 ES$^+$ (M + H) | 2.23 (s, 3H), 2.26 (s, 3H), 4.05 (s, 3H), 4.31 (t, 3H), 4.66 (t, 3H), 6.00 (s, 1H), 6.74 (d, 2H), 7.00 (d, 1H), 7.04 (d, 2H), 7.58 (d, 1H) |
| 106 | 4-carbamoyl phenoxyethyl | 45% from 36 | — | 409.9 ES$^+$ (M + H) | 2.23 (s, 3H), 4.06 (s, 3H), 4.41 (t, 2H), 4.70 (t, 2H), 5.68 (br s, 2H), 6.00 (s, 1H), 6.89 (d, 2H), 7.01 (d, 1H), 7.58 (d, 1H), 7.75 (d, 2H) |
| 107 | 2,3,5,6-tetrafluoro phenoxyethyl | 38% from 36 | — | 438.8 ES$^+$ (M + H) | 2.34 (s, 3H), 4.05 (s, 3H), 4.63-4.68 (m, 4H), 6.03 (s, 1H), 6.76 (m$_c$, 1H), 7.00 (d, 1H), 7.58 (d, 1H) |
| 108 | 1-naphthyloxy ethyl | 54% from 36 | — | 416.9 ES$^+$ (M + H) | 2.07 (s, 3H), 4.05 (s, 3H), 4.54 (t, 2H), 4.85 (t, 2H), 5.89 (s, 1H), 6.81 (d, 1H), 6.99 (d, 1H), 7.29-7.46 (m, 4H), 7.56 (d, 1H), 7.75 (d, 1H), 7.87 (d, 1H) |
| 109 | 2-pyridyloxyethyl | 43% from 36 | — | 367.9 ES$^+$ (M + H). | 2.26 (s, 3H), 4.03 (s, 3H), 4.40 (t, 2H), 4.61 (t, 2H), 6.00 (s, 1H), 6.17 (t, 1H), 6.59 (d, 1H), 6.98 (d, 1H), 7.37 (t, 1H), 7.55 (d, 1H), 7.59 (d, 1H). |
| 110 | 3-pyridyloxyethyl | 39% from 36 | — | 367.9 ES$^+$ (M + H). | 2.26 (s, 3H), 4.06 (s, 3H), 4.40-4.43 (m, 2H), 4.67-4.70 (m, 2H), 6.01 (s, 1H), 7.00-7.01 (m, 1H), 7.19 (br s, 2H), 7.57-7.58 (m, 1H), 8.23 (br s, 1H), 8.32 (br s, 1H) |
| 111 | 4-pyridyloxyethyl | 43% from 36 | — | 367.9 ES$^+$ (M + H). | 2.24 (s, 3H), 4.05 (s, 3H), 4.41 (m$_c$, 2H), 4.68 (m$_c$, 2H), 6.01 (s, 1H), 6.79 (d, 2H), 7.00 (d, 1H), 7.57 (d, 1H), 8.42 (br s, 2H) |
| 112 | 1-imidazolylethyl | 34% from 36 | — | 340.9 ES$^+$ (M + H) | 2.31 (s, 3H), 4.04 (s, 3H), 4.40 (t, 2H), 4.59 (t, 2H), 6.02 (s, 1H), 7.00 (d, 1H), 7.12 (br s, 1H), 7.18 (br s, 1H), 7.59 (d, 1H), 7.80 (br s, 1H). |
| 113 | 1-benzimidazolyl propyl | 87% from 37 | — | 404.9 ES$^+$ (M + H) | 2.36 (s, 3H), 2.37 (quintet, 2H), 4.06 (s, 3H), 4.28 (t, 2H), 4.59 (t, 2H), 6.05 (s, 1H), 7.01 (d, 1H), 7.27-7.32 (m, 2H), 7.47-7.50 (m, 1H), 7.59 (d, 1H), 7.80-7.83 (m, 1H), 8.06 (br s, 1H) |

Biological Activity
1. Determination of $EC_{50}$ (Blockade)

The effectiveness of the generated compounds in blocking the Kv1.3 current was assayed on L929 cells stably expressing mKv1.3 or on activated human T cells. The generation of this cell line has been previously described (Grissmer et al. (1995) *Mol. Pharmacol.* 45: 1227). The cells were grown in Dulbecco's modified Eagle's medium containing 10% fetal calf serum, 2 mM L-glutamine, 1 mM $Na^+$ pyruvate, 100 units/ml penicillin, 100 µg/ml streptomycin and 250 µg G418 (to keep them under selection pressure). The cells were studied in the whole-cell configuration of the patch-clamp technique. The holding potential in all experiments was −80 mV. Currents were recorded in normal Ringer solution (160 mM NaCl, 4.5 mM KCl, 2 mM $CaCl_2$, 1 mM $MgCl_2$, 10 mM HEPES, pH 7.4, 290-310 mOsm) with an internal pipette solution containing 134 mM KF, 2 mM $MgCl_2$, 10 mM HEPES, 10 mM EGTA (pH 7.2, 290-310 mOsm). If currents exceeded 2 nA 60-80% series resistance compensation was used. 200-ms depolarising pulses to 40 mV were applied every 30 s (Grissmer at al. (1995) *Mol. Pharmacol.* 45: 1227). Each compound was tested twice at two to five different concentrations. $K_d$ values were determined by normalizing the reduction of the area under the current curve to the area under the current curve of the control current in the absence of drug and fitting the resulting normalized values to the Hill equation.

The results of the determination are set out in Tables 5, 7, 8 and 9 below. Those compounds less active at Kv1.3 are still of interest as being potentially selective for Kv channels other than Kv1.3.

2. Determination of $EC_{50}$ (Proliferation)

[$^3$H]-thymidine incorporation is a widely used test to assay the proliferative activity of human and rodent lymphocytes. As cells divide [$^3$H]-thymidine will be incorporated into the newly synthesised DNA of the resulting daughter cells. The faster cells grow the more radioactive [$^3$H]-thymidine will be incorporated. Any compound that inhibits lymphocytes proliferation will reduce the uptake of radioactivity by the cells treated with it compared to the untreated controls.

The selected compounds were tested to determine its ability to inhibit [$^3$H]-thymidine incorporation and the results are set out in table 6 below. Resting peripheral blood mononuclear cells from healthy volunteers were seeded at 2×10$^5$ cells per well in medium (RPMI 1640 supplemented 10% fetal calf serum, 2 mM glutamine, 1 mM sodium pyruvate, 1% nonessential amino acids, 100 units/ml penicillin, 100 µg/ml streptomycin and 50 µM β-mercaptoethanol) in flat-bottom 96 well plates (final volume 200 µl). Cells were pre-incubated with the compound of example 2 for 60 min, and were stimulated with 5 ng/ml anti-CD3 Ab for 48 h. [$^3$H]-Thymidine (1 µCi per well) was added for the last 6 h. Cells were harvested onto glass fibre filters and radioactivity measured in a scintillation counter. All experiments were done in triplicate. Results are normalised for maximum [$^3$H]-thymidine incorporation by control. The untreated control had a normalised [$^3$H]-thymidine incorporation of 1.

TABLE 8

Biological Activity (Blockade) for compounds of formula I
(X = O, $R_1$ = $R_2$ = H, $R_3$ = Me, $R_4$ = —$OR_a$, and $R_5$ = —$OR_b$)

| Compd | $R_a$ | $R_b$ | $EC_{50}$ (nM) blockade |
|---|---|---|---|
| 41 | Me | 3-(phenyl)propyl | 68 |
| 73 | Me | 4-fluorophenoxyethyl | 140 |
| 70 | Me | 3-methylphenoxyethyl | 170 |
| 65 | Me | 4-chlorophenoxyethyl | 290 |
| 68 | Me | 2,3,5,6-tetrafluoro phenoxyethyl | 350 |
| 55 | Me | 4-bromobenzyl | 400 |
| 10 | 5-(phenyl)pentyl | Me | 430 |
| 72 | Me | 2-fluorophenoxyethyl | 430 |
| 80 | Me | 3-(phenoxy)propyl | 440 |
| 64 | Me | phenoxyethyl | 500 |
| 42 | Me | 4-(phenyl)butyl | 500 |
| 43 | Me | 5-(phenyl)pentyl | 500 |
| 9 | 4-(phenyl)butyl | Me | 500 |
| 69 | Me | 2-methylphenoxyethyl | 520 |
| 4 | (1-naphthyl)methyl | Me | 500 |
| 60 | Me | (4-trifluoromethoxy)benzyl | 550 |
| 66 | Me | 5-bromo-2,4,-difluorophenoxy ethyl | 590 |
| 52 | Me | 3-nitrobenzyl | 590 |
| 71 | Me | 4-methylphenoxethyl | 600 |
| 45 | Me | 2-chlorobenzyl | 700 |
| 8 | 3-(phenyl)propyl | Me | 710 |
| 21 | 4-fluorobenzyl | Me | 730 |
| 53 | Me | 4-fluorobenzyl | 730 |
| 22 | 4-chlorobenzyl | Me | 800 |
| 48 | Me | 3-fluorobenzyl | 1000 |
| 82 | Bn | Bn | 1200 |
| 12 | 2-chlorobenzyl | Me | 1200 |
| 15 | 3-fluorobenzyl | Me | 1260 |
| 16 | 3-chlorobenzyl | Me | 1400 |
| 19 | 3-(trifluoromethoxy)benzyl | Me | 1450 |
| 39 | Me | benzyl | 1540 |
| 78 | Me | 4-pyridyloxy ethyl | 1570 |
| 54 | Me | 4-chlorobenzyl | 1570 |
| 11 | 2-fluorobenzyl | Me | 1700 |
| 44 | Me | 2-fluorobenzyl | 1700 |
| 14 | 2-phenylbenzyl | Me | 1900 |
| 6 | benzyl | Me | 1900 |
| 46 | Me | 2-methylbenzyl | 2000 |
| 13 | 2-methylbenzyl | Me | ~2000 |
| 67 | Me | 4-carbamoylphenoxyethyl | 2200 |
| 20 | 3-nitrobenzyl | Me | 2200 |
| 77 | Me | 3-pyridyloxyethyl | 2500 |
| 47 | Me | 2-phenylbenzyl | 4000 |
| 49 | Me | 3-chlorobenzyl | 4000 |
| 50 | Me | 3-methylbenzyl | ~5000 |
| 17 | 3-methylbenzyl | Me | 5000 |
| 79 | Me | 1-imidazolyl ethyl | 5300 |
| 25 | 4-isopropylbenzyl | Me | 7500 |
| 61 | Me | 4-benzyloxybenzyl | 8200 |
| 56 | Me | (4-trifluoromethyl)benzyl | >1 uM |
| 40 | Me | phenethyl | >1 uM |
| 38 | Me | (2-napthyl)methyl | >1 uM |
| 57 | Me | 4-isopropylbenzyl | >1 uM |
| 24 | (4-trifluoromethyl)benzyl | Me | >1 uM |
| 76 | Me | 2-pyridyloxyethyl | >10 uM |
| 59 | Me | 4-phenylbenzyl | >10 uM |
| 62 | Me | (4-benzoyl)benzyl | >10 uM |
| 63 | Me | 4-carboxybenzyl | >10 uM |
| 27 | 4-phenylbenzyl | Me | >10 uM |
| 31 | 4-(benzoyl)benzyl | Me | >10 uM |
| 29 | 4-(trifluoromethoxy)benzyl | Me | >10 uM |
| 32 | 4-carboxybenzyl | Me | >10 uM |
| 30 | 4-benzyloxybenzyl | Me | >10 uM |
| 58 | Me | 4-(t-butyl)benzyl | >10 uM |
| 26 | 4-(t-butyl)benzyl | Me | >10 uM |
| 83 | 3-(phenyl)propyl | 3-(phenyl)propyl | >10 uM |
| 51 | Me | 3-carboxybenzyl | >10 uM |

TABLE 9

Biological Activity (Proliferation) Data for selected compounds

| Compd | EC50 (nM) proliferation |
|---|---|
| 41 | 1000 |
| 55 | 2500 |
| 22 | 2500 |

TABLE 10

Biological Activity for 7-7 dimers of formula V

| COMPD | LINKER | $EC_{50}$ (nM) blockade |
|---|---|---|
| 90 | —$(CH_2)_n$—, n = 4 | not available |
| 91 | —$(CH_2)_n$—, n = 5 | 215 |
| 92 | —$(CH_2)_n$—, n = 6 | 350 |
| 93 | —$(CH_2)_n$—, n = 7 | 3500 |
| 94 | m-xylyl | >5000 |
| 95 | p-xylyl | >>5000 |

TABLE 11

Biological Activity for 4-4 dimers of formula IV

| COMPD | LINKER | $EC_{50}$ (nM) blockade |
|---|---|---|
| 84 | —$(CH_2)_n$—, n = 4 | 175 |
| 85 | —$(CH_2)_n$—, n = 5 | 95 |
| 86 | —$(CH_2)_n$—, n = 6 | >1000 |
| 87 | —$(CH_2)_n$—, n = 7 | 5000 |
| 88 | m-xylyl | 780 |
| 89 | p-xylyl | >>1000 |

TABLE 12

Biological Activity for 7-6 dimer - Compound 76

| COMPD | $EC_{50}$ (nM) blockade |
|---|---|
| 98 | 190 |

TABLE 13

Biological Activity (Blockade) for compounds of formula VI (X = O, $R_1 = R_2$ = H, $R_4$ = —$OR_a$, and $R_5$ = —$OR_b$)

| Compd | $R_a$ | $R_b$ | $EC_{50}$ (nM) blockade |
|---|---|---|---|
| 102 | Me | 4-(phenyl)butyl | 330 |
| 103 | Me | 5-(phenyl)pentyl | 340 |
| 100 | 5-(phenyl)pentyl | Me | 360 |
| 108 | Me | 1-naphthyloxyethyl | 360 |
| 104 | Me | 2-fluorophenoxyethyl | 560 |
| 101 | Me | 3-(phenyl)propyl | 580 |
| 99 | 4-(phenyl)butyl | Me | 600 |
| 105 | Me | 4-methylphenoxyethyl | 1800 |
| 107 | Me | 2,3,5,6-tetrafluoro phenoxyethyl | 2100 |
| 110 | Me | 3-pyridyloxyethyl | 2800 |
| 111 | Me | 4-pyridyloxyethyl | 10800 |
| 106 | Me | 4-carbamoylphenoxyethyl | >10 uM |
| 112 | Me | 1-imidazolylethyl | >10 uM |
| 109 | Me | 2-pyridyloxyethyl | >10 uM |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of the formula

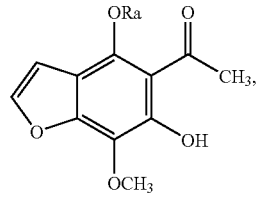

or a salt thereof,
wherein $R_a$ is —$(CH_2)_n$-optionally substituted aryl or optionally substituted heteroaryl, or —$(CH_2)_n$—O-optionally substituted aryl or optionally substituted heteroaryl group, where n is 1, 2, 3, 4 or 5.

2. A compound according to claim 1 or a salt thereof, wherein $R_a$ is —$(CH_2)_n$-optionally substituted aryl or optionally substituted heteroaryl.

3. A compound according to claim 2, or a salt thereof, wherein the —$(CH_2)_n$-optionally substituted aryl group is selected from 1-naphthylmethyl, 2-naphthylmethyl, benzyl, phenethyl, phenylpropyl, phenylbutyl, phenylpentyl, 2-fluorobenzyl, 2-chlorobenzyl, 2-methylbenzyl, 2-phenylbenzyl, 3-fluorobenzyl, 3-chlorobenzyl, 3-methylbenzyl, 3-methoxybenzyl, 3-trifluoromethoxybenzyl, 3-nitrobenzyl, 4-fluorobenzyl, 4-chlorobenzyl, 4-bromobenzyl, 4-trifluoromethylbenzyl, 4-isopropylbenzyl, 4-tertbutylbenzyl, 4-phenylbenzyl, 4-methoxybenzyl, 4-trifluoromethoxybenzyl, 4-benzyloxybenzyl, 4-benzoylbenzyl, and 4-carboxybenzyl.

4. A compound of the formula

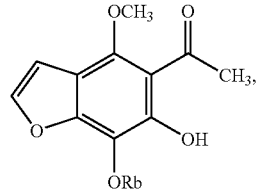

or a salt thereof,
wherein $R_b$ is —$(CH_2)_n$-optionally substituted aryl or optionally substituted heteroaryl, or —$(CH_2)_n$—O-optionally substituted aryl or optionally substituted heteroaryl, where n is 1, 2, 3, 4 or 5.

5. A compound according to claim 4, or a salt thereof, wherein the —$(CH_2)_n$-optionally substituted aryl or optionally substituted heteroaryl, or —$(CH_2)_n$—O-optionally substituted aryl or optionally substituted heteroaryl group, is selected from 2-naphthylmethyl, benzyl, phenethyl, 3-(phenyl)propyl, 4-(phenyl)butyl, 5-(phenyl)pentyl, 2-fluorobenzyl, 2-chlorobenzyl, 2-methylbenzyl, 2-phenylbenzyl, 3-fluorobenzyl, 3-chlorobenzyl, 3-methylbenzyl, 3-carboxybenzyl, 3-nitrobenzyl, 4-fluorobenzyl, 4-chlorobenzyl, 4-bromobenzyl, 4-trifluoromethylbenzyl, 4-isopropylbenzyl, 4-tertbutylbenzyl, 4-phenylbenzyl, 4-trifluoromethoxybenzyl, 4-benzyloxybenzyl, 4-benzoylbenzyl, 4-carboxybenzyl, phenoxyethyl, 4-chlorophenoxyethyl, 5-bromo-2,4-difluorophenoxyethyl, 4-carbamoylphenoxyethyl, 2,3,5,6-tetrafluorophenoxyethyl, 2-methylphenoxyethyl, 3-methylphenoxyethyl, 4-methylphenoxyethyl, 2-fluorophenoxyethyl, 4-fluorophenoxyethyl, 1-naphthyloxyethyl, 2-naphthyloxyethyl, 2-pyridyloxyethyl, 3-pyridyloxyethyl, 4-pyridyloxyethyl, 1-imidazolylethyl, phenoxypropyl, 3-(1-benzimidazolyl)propyl.

6. A compound according to claim 4, or a salt thereof, wherein the —(CH$_2$)$_n$-optionally substituted aryl group is 3-(phenyl)propyl.

7. A compound according to claim 4, wherein the —(CH$_2$)$_n$—O-optionally substituted aryl group is 4-fluorophenoxyethyl or 3-methylphenoxyethyl.

8. A compound of formula

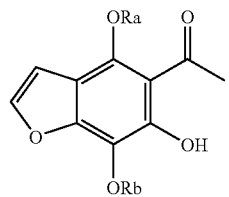

or a salt thereof,
where R$_a$ and R$_b$ are the same and are selected from benzyl and 3-(phenyl)propyl.

9. A compound of formula IV

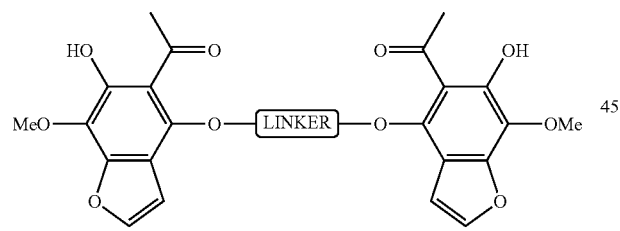

Formula IV or a salt thereof,
wherein the linker group is —(CH$_2$)$_n$— where n=4, 5, 6 or 7, or divalent m-xylyl or p-xylyl.

10. A compound of formula V

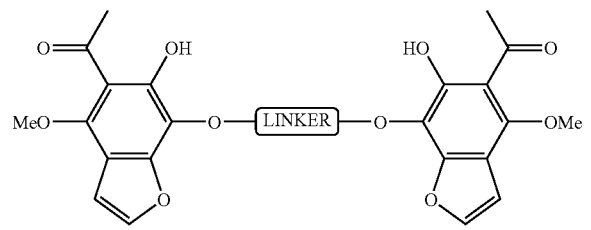

Formula V or a salt thereof,
wherein the linker group is —(CH$_2$)$_n$— where n=4, 5, 6, or 7 or divalent m-xylyl or p-xylyl.

11. A pharmaceutical composition comprising a therapeutically effective amount of one or more of the compounds according to any one of claims 1 to 4, or salts thereof, and optionally a pharmaceutically acceptable carrier or diluent.

12. A pharmaceutical composition according to claim 11 which further comprises one or more immunosuppressive compounds.

13. A pharmaceutical composition according to claim 12, wherein the immunosuppressive compound is selected from azathioprine, brequinar sodium, deoxyspergualin, mizaribine, mycophenolic acid morpholino ester, cyclosporin, FK-506 and rapamycin.

14. A method of preventing transplantation rejection of organs or tissue comprising administering to a patient a therapeutically effective amount of a compound according to any one of claims 1 to 8 or a pharmaceutically acceptable salt thereof.

15. A method for the treatment of multiple sclerosis comprising administering to a patient a therapeutically effective amount of a compound according to any one of claims 1 to 8, or a pharmaceutically acceptable salt thereof.

16. A process for preparing a compound of formula I, or salts thereof, comprising subjecting a compound of formula VI

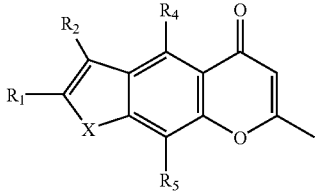

Formula VI to alkaline hydrolysis for a time and under conditions sufficient to form a compound of formula I, wherein R$_1$ and R$_2$ are independently selected from hydrogen, halo, C$_{1-6}$ alkyl, halo C$_{1-6}$ alkyl, phenyl and benzyl;

R$_3$ is an unsubstituted or halo substituted C$_{1-6}$ alkyl;

R$_4$ and R$_5$ are independently selected from C$_{1-10}$ alkyl, C$_{2-10}$ alkenyl; C$_{2-10}$ alkynyl, C$_{3-10}$ alkoxy, C$_{2-10}$ alkenyloxy and C$_{2-10}$ alkynyloxy;

and one of R$_4$ and R$_5$ is optionally substituted with one or more substituents selected from halo, aryl, aryloxy, heteroaryl and heteroaryloxy, the aryl, aryloxy, heteroaryl and heteroaryloxy substituents being optionally substituted;

and where the other of R$_4$ and R$_5$ is substituted with an aryl, aryloxy, heteroaryl or heteroaryloxy group, the group being optionally substituted, X is O, S or NR$_7$ where R$_7$ is independently selected from hydrogen, C$_{1-6}$ alkyl and halo C$_{1-6}$ alkyl.

17. A process according to claim 16, wherein the compound of formula I is dissolved in ethanol, contacted with sodium or potassium hydroxide and the resultant mixture heated at reflux.

18. A compound of formula VI,

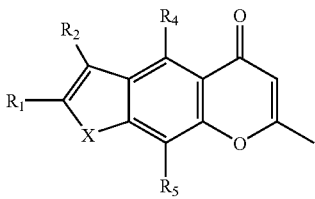

Formula VI or a salt thereof,
wherein $R_1$ and $R_2$ are independently selected from hydrogen, halo, $C_{1-6}$ alkyl, halo $C_{1-6}$ alkyl, phenyl and benzyl;
$R_4$ and $R_5$ are independently selected from $C_{1-10}$ alkyl, $C_{2-10}$ alkenyl; $C_{2-10}$ alkynyl, $C_{1-10}$ alkoxy, $C_{2-10}$ alkenyloxy and $C_{2-10}$ alkynyloxy;
and one of $R_4$ and $R_5$ is optionally substituted with one or more substituents selected from halo, aryl, aryloxy, heteroaryl and heteroaryloxy, the aryl, aryloxy, heteroaryl and heteroaryloxy substituents being optionally substituted;
and where the other of $R_4$ and $R_5$ is substituted with an aryl, aryloxy, heteroaryl or heteroaryloxy group, the group being optionally substituted,
X is O, S or $NR_7$ where $R_7$ is independently selected from hydrogen, $C_{1-6}$ alkyl and halo $C_{1-6}$ alkyl;
provided that $R_4$ can not be unsubstituted benzyloxy when X is O, $R_1$ and $R_2$ are hydrogen and $R_5$ is methoxy.

19. The method of claim 14, wherein the organ or tissue is selected from heart, kidney, liver, lung, bone marrow, cornea, pancreas, intestinum tenue, limb, muscle, nervus, medulla ossium, duodenum, small-bowel, skin, and pancreatic islet-cell.

20. The method of claim 14, wherein the transplantation is xeno transplantation.

* * * * *